United States Patent [19]

Corbet et al.

[11] Patent Number: 4,618,599

[45] Date of Patent: Oct. 21, 1986

[54] SYNERGISTINE DERIVATIVES HAVING ANTI-BACTERIAL ACTIVITY AND THEIR USE

[75] Inventors: Jean-Pierre Corbet, Ecully; Claude Cotrel, Paris; Daniel Farge, Thiais; Jean-Marc Paris, Vaires sur Marne, all of France

[73] Assignee: Rhone-Poulenc Sante, Courbevoie, France

[21] Appl. No.: 630,288

[22] Filed: Jul. 12, 1984

[30] Foreign Application Priority Data

Jul. 13, 1983 [FR] France ................ 83 11705

[51] Int. Cl.$^4$ .................. A61K 37/02; C07K 5/12
[52] U.S. Cl. .................. 514/11; 530/317
[58] Field of Search .............. 260/112.5 R; 514/11

[56] References Cited

PUBLICATIONS

J. Preud'homme, P. Tarridec and A. Belloc, pp. 585–591, (1967).
Chem. Abstr. vol. 99, (1983) 212905.
Chem. Abstr. vol. 76, (1972) 127404.
Chem. Abstr. vol. 63, (1965) 13408.
Merck Index, 9th Edition (1976), "Mikamycin and Virginiamycin".
Preud'homme et al. Article.
Mutton et al. (Chemotherapy 29), (1983).
Mattei et al., La Presse Medicale 29, 1789 (1984).
Rollmann et al., Pharm. Acta Helv. 50(12) 455(1975).

*Primary Examiner*—Delbert R. Phillips
*Attorney, Agent, or Firm*—Stevens, Davis, Miller & Masher

[57] ABSTRACT

The invention provides new synergistine derivatives of the formula:

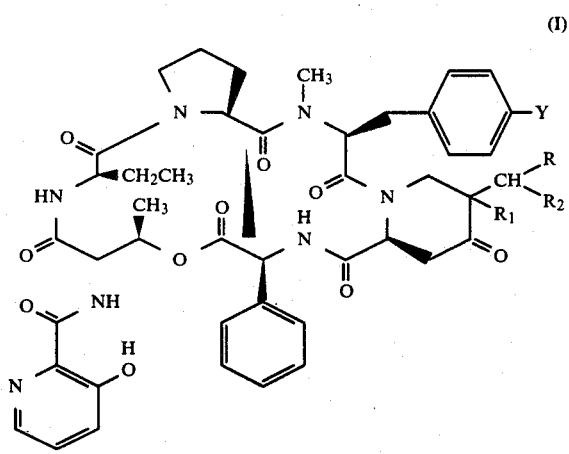

(I)

in which Y=H or N(CH$_3$)$_2$ and
(a) R$_1$ and R$_2$=H and R=pyrrolidin-3-ylthio or piperidin-3-ylthio or piperidin-4-ylthio (optionally substituted by alkyl), or altenatively R=alkylthio substituted by 1 or 2 SO$_3$H radicals or alkylamino or dialkylamino radicals (optionally substituted) or by 1 or 2 piperazino rings (optionally substituted) or morpholino, thiomorpholino, piperidino, pyrrolidin-1-yl, piperidin-2-yl, piperidin-3-yl or piperidin-4-yl or pyrrolidin-2-yl or pyrrolidin-3-yl rings (these last 5 rings being optionally substituted by alkyl), or
(b) R$_1$ and R$_2$ form a bond and R=pyrrolidin-3-ylamino, piperidin-3-ylamino or piperidin-4-ylamino, pyrrolidin-3-yloxy, piperidin-3-yloxy or piperidin-4-yloxy, pyrrolidin-3-ylthio, piperidin-3-ylthio or piperidin-4-ylthio (optionally substituted by alkyl), or alternatively R=alkylamino, alkoxy or alkylthio substituted by 1 or 2 SO$_3$H radicals, alkylamino or dialkylamino radicals (optionally substituted) or trialkylammonio or imidazol-4-yl or imidazol-5-yl radicals or by 1 or 2.piperazino rings (optionally substituted by alkyl) or morpholino, thiomorpholino, piperidino, pyrrolidin-1-yl, piperidin-2-yl, piperidin-3-yl or piperidin-4-yl or pyrrolidin-2-yl or pyrrolidin-3-yl rings (these last two rings being optionally substituted by alkyl), and their salts, their preparation, and the pharmaceutical compositions in which they are present. These compounds are useful as anitbacterial agents.

12 Claims, No Drawings

SYNERGISTINE DERIVATIVES HAVING ANTI-BACTERIAL ACTIVITY AND THEIR USE

This invention relates to synergistine derivatives and their use.

Pristinamycin and virginiamycin are known synergistine derivatives having antibacterial activity, see J. Preud'homme et al., Bull. Soc. Chim. Fr., 2, 585–91 (1968).

The present invention provides new synergistine derivatives of the formula:

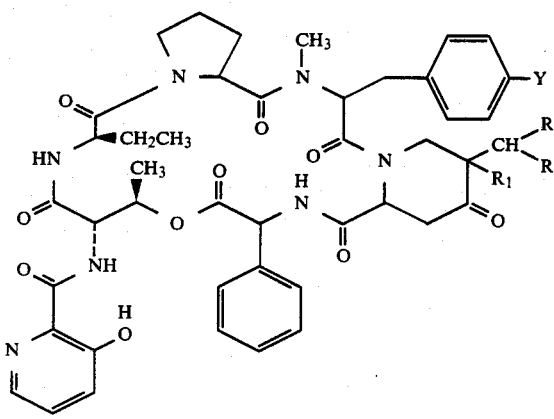
(I)

in which Y represents a hydrogen atom or a dimethylamino radical and (a) $R_1$ and $R_2$ each represent a hydrogen atom and R represents a pyrrolidin-3-ylthio or piperidin-3-ylthio or piperidin-4-ylthioradical (these radicals being optionally substituted by an alkyl radical), or alternatively R represents an alkylthio radical substituted by one or two hydroxysulphonyl radicals or alkylamino or dialkylamino radicals (optionally substituted by a mercapto or dialkylamino radical) or by one or two rings chosen from piperazino (optionally substituted by an alkyl or mercaptoalkyl radical), morpholino, thiomorpholino, piperidino, pyrrolidin-1-yl, piperidin-2-yl, piperidin-3-yl or piperidin-4-yl and pyrrolidin-2-yl or pyrrolidin-3-yl (these last five rings being optionally substituted on the nitrogen atom by an alkyl radical), or (b) $R_1$ and $R_2$ together form a valence bond and R represents a pyrrolidin-3-ylamino, piperidin-3-ylamino or piperidin-4-ylamino, pyrrolidin-3-yloxy, piperidin-3-yloxy or piperidin-4-yloxy, pyrrolidin-3-ylthio, piperidin-3-ylthio or piperidin-4-ylthio radical (these radicals being optionally substituted on the nitrogen atom of the ring by an alkyl radical), or alternatively R represents an alkylamino, alkoxy or alkylthio radical substituted by one or two hydroxysulphonyl radicals, alkylamino or dialkylamino radicals (optionally substituted by a dialkylamino radical) or trialkylammonio or imidazol-4-yl, or imidazol-5-yl radicals or by one or two rings chosen from piperazino (optionally substituted by an alkyl or mercaptoalkyl radical), morpholino, thiomorpholino, piperidino, pyrrolidin-1-yl, piperidin-2-yl, piperidin-3-yl or piperidin-4-yl and pyrrolidin-2-yl or pyrrolidin-3-yl (these last two rings being optionally substituted on the nitrogen atom by an alkyl radical), it being understood that the alkyl radicals and alkyl portions which have been mentioned above and which will be mentioned below contain 1 to 5 carbon atoms, unless started otherwise, and have a linear or branched chain.

The compounds of formula (I) in which $R_1$ and $R_2$ form a valence bond can exist in 2 isomeric forms; both these isomers and their mixture fall within the scope of the present invention.

A/ According to a feature of the invention, the compounds of the formula (I) in which Y is defined as above and the other symbols are defined as above under (a) can be prepared by reacting a compound of the formula:

$$R'-H \qquad (II)$$

in which R' has the definition of R given above under (a), with a compound of the formula:

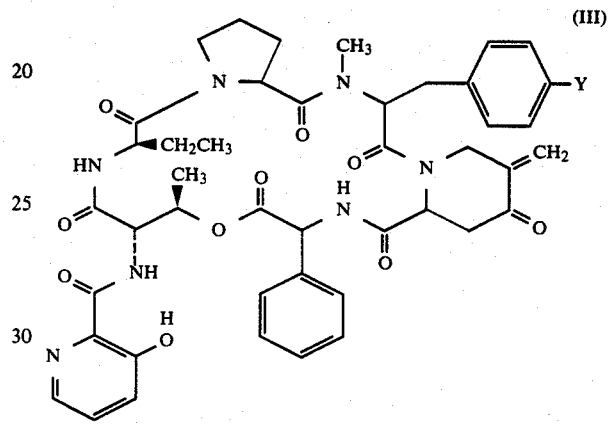
(III)

in which Y is defined as above.

The reaction is generally carried out in an organic solvent e.g. an alcohol such as methanol or a chlorinated solvent such as chloroform, or a mixture of these solvents, at a temperature of between 0° C. and the reflux temperature of the reaction mixture, preferably at a temperature of the order of 20° C.

Compounds of the formula (III) can be prepared by reacting an alkali metal borohydride, in the presence of a strong organic acid, with a compound of the formula:

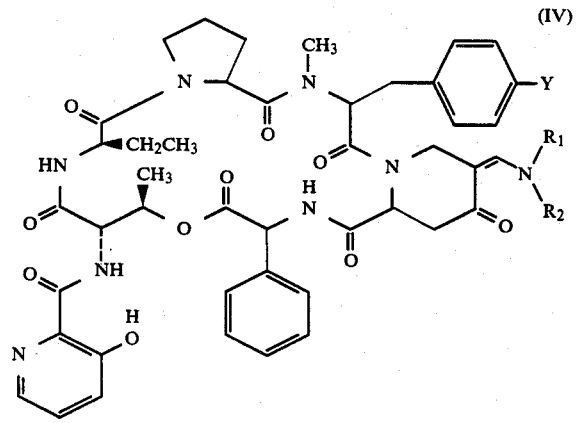
(IV)

in which Y is defined as above and $R_1$ and $R_2$ are alkyl radicals containing 1 to 4 carbon atoms or together form, with the nitrogen atom to which they are bonded, a 5-membered or 6-membered heterocycle optionally containing another heteroatom chosen from oxygen, nitrogen or sulphur.

The reaction is generally carried out with sodium borohydride or cyanoborohydride in an organic solvent e.g. an ether such as tetrahydrofuran or an alcohol such as isopropanol, in the presence of a strong organic acid such as trifluoroacetic acid, at a temperature of between 0° C. and the reflux temperature of the reaction mixture, preferably at a temperature of the order of 20° C.

The compounds of the formula (IV) can be obtained by reacting a compound of the formula:

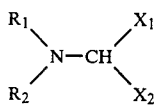
(V)

in which $R_1$ and $R_2$ are defined as above and $X_1$ and $X_2$, which are identical or different, represent an alkoxy radical or a substituted amino radical defined in the same way as $-NR_1R_2$, with a compound of the formula:

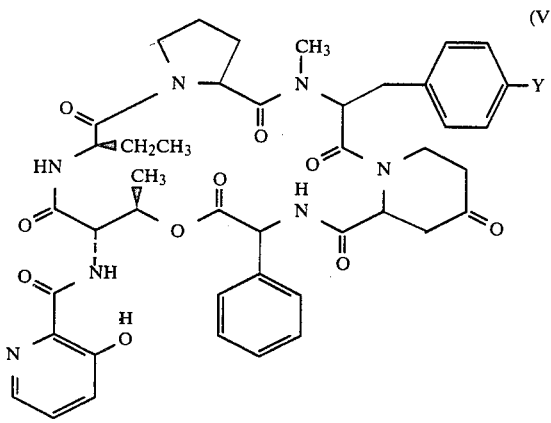
(VI)

in which Y is defined as above, i.e. pristinamycin $I_A$ [Y=N(CH$_3$)$_2$] or virginiamycin S (Y=H).

It is preferable to use a reactant of the formula (V) in which $X_1$ and/or $X_2$ are chosen so that the substituted amino radical is identical to the group $-NR_1R_2$ present on the molecule.

In practice, it is advantageous to react tert.-butoxybis(dimethylamino)methane with the compound of the formula (VI), in an organic solvent such as a chlorinated solvent like 1,2-dichloroethane or an amide (e.g. dimethylformamide), at a temperature of between 0° and 80° C., preferably at a temperature of the order of 20° C.

The compounds of the formula (V) can be prepared by the methods described by H. BREDERECK et al., Chem. Ber., 101, 41 and 3058 (1968) and Chem. Ber., 106, 3725 (1973).

B/ According to a further feature of the invention, the compounds of the formula (I) in which Y is defined as above and the other symbols are defined as above under (b), except that R cannot represent a pyrrolidin-3-yloxy, piperidin-3-yloxy or piperidin-4-yloxy or alkoxy radical (optionally substituted as defined under (b)), are prepared by reacting a compound of the formula:

R''-H (VII)

in which R'' has the definition of R given above under (b), except that it cannot represent a pyrrolidin-3-yloxy, piperidin-3-yloxy or piperidin-4-yloxy or alkoxy radical (optionally substituted as defined under (b)), with a compound of the formula (IV) in which Y is defined as above and $R_1$ and $R_2$, which are identical or different, represent a hydrogen atom, a phenyl or pyridyl radical which is optionally substituted (by a dialkylamino radical of which the alkyl part contains 1 to 4 carbon atoms in a linear or branched chain), an alkyl radical containing 1 to 10 carbon atoms in a linear branched chain, which is optionally substituted (by a hydroxyl, mercapto, carboxyl, pyridyl or anilino radical or an alkylamino or dialkylamino radical of which at least one of the alkyl parts is itself substituted by a hydroxyl, mercapto, carboxyl or anilino radical), an alkenyl radical containing 3 or 4 carbon atoms or an alkynyl radical containing 3 or 4 carbon atoms, or alternatively $R_1$ and $R_2$ together form, with the nitrogen atom to which they are bonded, a 5-membered or 6-membered heterocycle optionally containing another heteroatom such as oxygen, sulphur or nitrogen (optionally substituted by an alkyl radical).

The reaction is carried out in an organic medium, in the presence of an acid (e.g. acetic acid or a mixture of acetic acid and catalytic quantities of trifluoroacetic acid), in the presence or absence of a solvent, at a temperature of between 0° and 50° C., preferably at a temperature of the order of 20° C.

If necessary, the solvents can be chosen from organic solvents such as ethers (tetrahydrofuran), alcohols (ethanol) or chlorinated solvents (e.g. methylene chloride or chloroform).

The compounds of the formula (IV) in which $R_1$ and $R_2$ are as defined above, except that they cannot have the meanings defined above for formula (IV) in process A/, can be obtained by transenamination by reacting an amine of the formula $HNR_1R_2$, in which $R_1$ and $R_2$ are as defined above, with an enamine of the formula (IV) in which $R_1$ and $R_2$ are as defined above in process A/.

C/ According to yet a further feature of the invention, the compounds of the formula (I) in which Y is defined as above and the other symbols are as defined above under (b) are prepared by reacting a compound of the formula:

R'''-H (VIII)

in which R''' is defined in the same way as R under (b), with a compound of the formula:

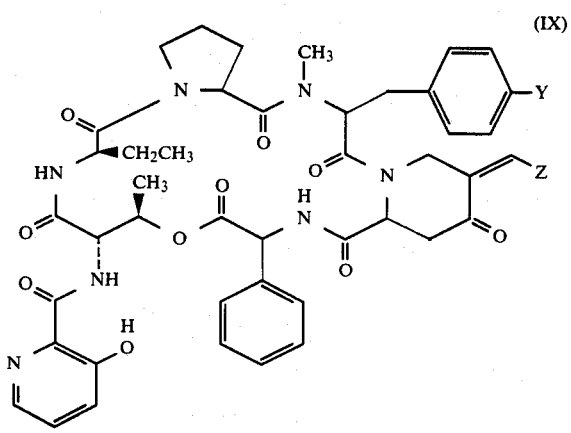

in which Y is defined as above and Z represents a halogen atom, a trimethylsilyloxy or dialkoxyphosphoryloxy radical or a radical of the formula:

 —OSO₂R₃ (IXa)

or

 —OCOR₄ (IXb)

in which formulae R₃ is an alkyl, trifluoromethyl or trichloromethyl radical or a phenyl radical optionally substituted by a halogen atom or by an alkyl or nitro radical, and R₄ is defined in the same way as R₃ or represents an alkylcarbonylmethyl, alkylcarbonylethyl, alkoxycarbonylmethyl, 2-alkoxycarbonylethyl or alkoxy radical. If Z represents a halogen atom, it is chosen from chlorine and bromine.

The reaction is generally carried out in an organic solvent e.g. an ether such as tetrahydrofuran, an alcohol such as ethanol or a chlorinated solvent (e.g. methylene chloride or chloroform), at a temperature of the order of 20° C. The reaction may be carried out in a basic medium, e.g. in the presence of an alkali metal hydride or an alkali metal alcoholate (e.g. sodium ethylate or potassium tert.-butylate).

If R‴ is other than substituted alkoxy or heterocyclyloxy, the reaction can also be carried out either in a neutral medium, at a temperature of between 0° and 50° C., in one of the above-mentioned solvents, or in an acid medium under identical conditions to those described above for process B/.

The compounds of the formula (IX) can be prepared by acid hydrolysis of compounds of the formula (IV) to give a compound of the formula:

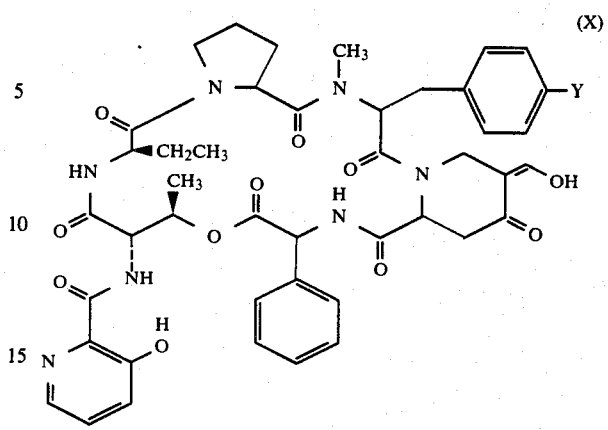

this being followed by: either (α) reaction with a compound of the formula:

 Z'-X (XI)

in which X represents a halogen atom and Z' has the definition given above for Z, except that it cannot represent a halogen atom, or (β) reaction with a halogenating agent, e.g. a compound of the formula:

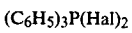 (C₆H₅)₃P(Hal)₂ (XII)

in which Hal represents a chlorine or bromine atom, to give a compound of the formula (IX) in which Z represents a halogen atom.

The hydrolysis of the compound of the formula (IV) to give the compound of the formula (X) is carried out with an aqueous solution of a mineral acid. The reaction is carried out using e.g. a 0.1N aqueous solution of hydrochloric acid at a temperature of the order of 20° C.

The reaction of the compound of the formula (XI) with the compound of the formula (X) is generally carried out in an organic solvent such as methylene chloride, in the presence of an acid acceptor such as an organic base, e.g. triethylamine, or an inorganic base, e.g. an alkali metal carbonate or bicarbonate such as sodium bicarbonate or potassium bicarbonate. The reaction temperature is generally between −20° and +20° C.

The reaction of the compound of the formula (XII) with the compound of the formula (X) is generally carried out in a chlorinated solvent such as methylene chloride, at a temperature of between −20° and +20° C.

The compounds of the formulae (II), (VII) and (VIII) can be prepared according to, or by analogy with, the methods described below in the examples, and especially according to:

G. G. URQUHART et al., Org. Synth., 21, 36 (1941)

A. I. VOGEL, J. Chem. Soc., 1822 (1948)

J. H. CHAPMAN and L. N. OWEN, J. Chem. Soc., 579 (1950)

H. R. SNYDER et al., J. Am. Chem. Soc., 69, 2672 (1947)

D. D. REYNOLDS et al., J. Org. Chem. 26, 5125 (1961)

in the case of a product of the general formula (II), (VII) or (VIII) in which R', R″ or R‴ represents a substituted alkylthio radical or a heterocyclylthio radical, or according to:

A. J. W. HEADLEE et al., J. Am. Chem. Soc., 55, 1066 (1933)

B. K. and K. N. CAMPBELL, J. Am. Chem. Soc., 60, 1372 (1938)

R. C. ELDERFIELD et al., J. Am. Chem. Soc., 68, 1579 (1946)

in the case of a product of the general formula (VII) or (VIII) in which R" or R'" represents a substituted alkoxy radical or a heterocyclyloxy radical, or according to:

J. Amer. Chem. Soc., 54, 1499 (1932) and J. Amer. Chem. Soc., 54, 3441 (1932) in the case where R" (or R'") is a substituted amino radical E. F. ELSLAGER et al., J. Med. Chem., 17, 99 (1974) and L. M. WERBEL et al., J. Het. Chem., 10, 363 (1973) in the case where R" (or R'") is a heterocyclylamino radical.

It is understood that, in the above methods, if R', R" or R'" contains an alkylamino radical capable of interfering with the reaction, this is protected beforehand by any known method which does not affect the rest of the molecule.

Likewise, if the radicals R', R" and R'" in the products of the general formulae (II), (VII) and (VIII) contain a secondary amine group, it may be necessary to protect it before reacting the corresponding products with the products of the general formulae (III), (IV) and (X) respectively. The protecting radical is removed after the reaction. This is carried out using any customary blocking means employed for protecting a secondary amine group, which does not affect the rest of the molecule and which is easily removed. It is particularly advantageous to use the trifluoroacetyl radical as the protecting radical; this can then be removed using an aqueous solution of an alkali metal bicarbonate such as sodium bicarbonate or potassium bicarbonate.

It is also understood that the products of the general formulae (IX) and (X) which can exist in 2 isomeric forms can be employed indiscriminately in one or other of these forms or a mixture thereof.

If the products of the general formula (I) have isomeric forms, these can be separated by any known method which does not affect the rest of the molecule, e.g. by high performance liquid chromatography.

The new synergistines of the formula (I) can be purified by the usual known methods such as crystallization, chromatography or successive extractions in an acidic or basic medium. For those skilled in the art who are familiar with the sensitivity of synergistines in an alkaline medium, it is obvious that the term "basic medium" is understood as meaning a medium which is just sufficiently alkaline to free the parent substance from its acid addition salt, i.e. a medium whose pH does not exceed 7.5 to 8.

The compounds of the formula (I) in which R represents a radical containing an amine group can be converted in to addition salts with acids by reaction with an acid in an organic solvent such as an alcohol, a ketone, an ester or a chlorinated solvent. The salt precipitates, if appropriate after concentration of its solution; it is separated off by filtration or decantation. The acid addition salts can also be obtained in the form of aqueous solutions by the addition of an aqueous solution of the corresponding acid to the compound of the formula (I).

The compounds of the formula (I) in which R represents a radical substituted by one or two hydroxysulphonyl radicals can be converted into metal salts or into addition salts with nitrogen bases in a manner analogous to that described above for the acid addition salts, except that the acid is replaced with a metal oxide or hydroxide or a nitrogen base.

Known synergistines obtained by fermentation are used by doctors for the treatment of many complaints caused by Gram-positive bacteria (of the genus Staphylococcus, Streptococcus, Pneumococcus or Enterococcus) and Gramnegative bacteria (of the genus Haemophilus, Gonococcus or Meningococcus). However, known compounds have the disadvantage of being insoluble in an aqueous medium and they can therefore only be administered orally, generally in the form of capsules, coated tablets or ordinary tablets. In view of this insolubility, it is impossible to use the known synergistines if the patient is not capable of swallowing; this is the case in particular in paediatrics and intensive care, whereas the spectrum of activity of these products would make them a valuable indication in a large number of circumstances, e.g. in cases of comatose septicaemia.

The compounds according to the invention have the considerable advantage of being able to be solubilized in water, in the form of salts, at therapeutically usable doses while at the same time retaining the general spectrum of activity of synergistines. They are especially active in vitro against *Staphylococcus aureus* Smith at concentrations of between 0.1 and 125 µg/ml.

Their toxicity is generally low. Their $LD_{50}$ is generally greater than 300 mg/kg, administered subcutaneously to mice.

For use in therapy, the compounds of the invention can be employed as such, i.e. in the form of the base, but for use in aqueous solution, which constitutes the main advantage of the products of the invention, it is particularly advantageous to employ their pharmaceutically acceptable salts, i.e. salts which are non-toxic at the use doses.

Pharmaceutically acceptable salts which may be mentioned are the addition salts with mineral acids, such as hydrochlorides, hydrobromides, sulphates, nitrates and phosphates, or with organic acids, such as acetates, propionates, succinates, maleates, fumarates, methanesulphonates, p-toluenesulphonates and isethionates, or substitution derivatives of these compounds. Other pharmaceutically acceptable salts which may be mentioned are the quaternary ammonium salts if R represents a trialkylammonio radical; these salts correspond to the anions of the salts listed above. Other pharmaceutically acceptable salts are the salts with alkali metals, such as the sodium, potassium and lithium salts, the salts with alkaline earth metals, such as the calcium or magnesium salt, the ammonium salt and the addition salts with organic nitrogen bases such as ethanolamine, diethanolamine, trimethylamine, triethylamine, methylamine, propylamine, diisopropylamine, N,N-dimethylethanolamine, benzylamine, dibenzylamine, dicyclohexylbenzylamine, N-benzyl-β-phenethylamine, N,N'-dibenzylethylenediamine, benzhydrylamine, arginine, leucine, lysine or N-methylglucamine.

Of particular value are the synergistines of the formula (I) in which: Y is a hydrogen atom or a dimethylamino radical and either $R_1$ and $R_2$ each represent a hydrogen atom and R represents a piperidin-4-ylthio radical unsubstituted or substituted by an alkyl radical, or an alkylthio radical substituted by one or two dialkylamino radicals, each optionally substituted by a mercapto radical, or alkylpiperazino or mercaptoalkylpiperazino radicals, or $R_1$ and $R_2$ together form a valence bond and R represents a piperidin-3-ylamino, piperidin-4-ylamino, piperidin-3-ylthio, or piperidin-4-ylthio unsubstituted or substituted on the nitrogen atom of the ring by an alkyl radical, or alternatively R represents an alkylamino, alkoxy or alkylthio radical substituted by one or two hydroxysulphonyl radicals, alkylamino or dialkylamino radicals, optionally substituted by another dialkylamino radical, or trialkylamino, imidazol-4-yl, imidazol-5-yl alkylpiperazino, morpholino, piperidino, pyrrolidinyl or N-alkylpyrrolidinyl radicals.

Among these products, those which are more especially active are the synergistine derivatives of the formula (I) in which: Y is a hydrogen atom or a dimethylamino radical and either $R_1$ and $R_2$ each represent a hydrogen atom and R represents an alkylpiperidin-4-ylthio radical or an alkylthio radical substituted by one or two dialkylamino or alkylpiperazino radicals, or $R_1$ and $R_2$ together form a valence bond and R represents a 1-alkylpiperidin-4-ylamino radical, or alternatively R represents a straight-chain alkylamino radical substituted by an alkylamino or dialkylamino radical of which the alkyl parts may form, with the nitrogen atom to which they are attached, a heterocycle chosen from pyrrolidin-1-yl, piperidino and 4-alkylpiperazino, or by a 1-alkylpyrrolidin-2-yl radical, or alternatively R represents a straight-chain alkylthio radical substituted by a 4-alkylpiperazino radical or represents a 5-dialkylaminopent-2-yl radical, and in particular the synergistines of the formula (I) in which: Y is a hydrogen atom or a dimethylamino radical and $R_1$ and $R_2$ each represent a hydrogen atom and R represents an alkylpiperidin-4-ylthio radical or an alkylthio radical substituted by one or two dialkylamino radicals or by an alkylpiperazino radical, or alternatively $R_1$ and $R_2$ together form a valence bond and R represents a 1-alkylpiperidin-4-ylamino radical, it being understood that the said alkyl portions and radicals are linear or branched and contain 1 to 3 carbon atoms each.

The following compounds are of more particular value:
5δ-(3-dimethylaminopropyl)thiomethylpristinamycin $I_A$;
5δ-[2-(4-methylpiperazin-1-yl)ethyl]thiomethylpristinamycin $I_A$;
5δ-[3-(4-methylpiperazin-1-yl)propyl]thiomethylpristinamycin $I_A$;
5δ-[1,3-bis(dimethylamino)prop-2-yl]thiomethylpristinamycin $I_A$;
5δ-(1-methylpiperidin-4-yl)aminomethylenepristinamycin $I_A$; and their pharmaceutically acceptable salts.

The Examples which follow, illustrate the invention.

The NMR spectra of the products described in these examples have general characteristics which are common to all the products and particular characteristics which are peculiar to each of the products according to the nature of the substituents Y, $R_1$ and $R_2$. In Example 1, the assignment of all the protons in the molecule is given; in the following examples, only the particular characteristics due to the variable radicals are mentioned. All the protons are designated according to the numbering indicated in the general formula (XIII) and recommended by J. O. ANTEUNIS et al. [Eur. J. Biochim., 58, 259 (1975)].

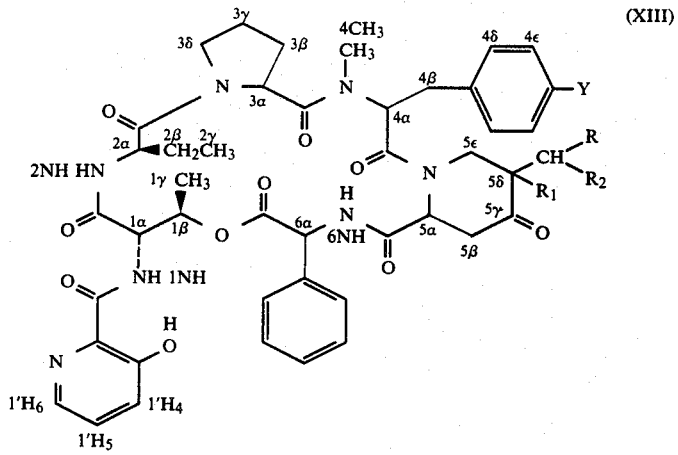

(XIII)

All the spectra were run at 250 MHz in deuterochloroform; the chemical shifts are expressed in ppm relative to the signal for tetramethylsilane. The abbreviations used below are as follows:

s=singlet
d=doublet
t=triplet
mt=multiplet
up=unresolved peaks
dd=doublet of doublets
dt=doublet of triplets
ddd=doublet of doublet of doublets
dddd=doublet of doublet of doublet of doublets In Examples 2 to 50, the following are given respectively in brackets: the chemical shift, the shape of the signal, the integration (number of protons, if appropriate with the percentage of isomer) and the assignment of the protons.

In the Examples which follow, "flash" chromatography is understood as meaning a purification technique which comprises using a short chromatography column and operating under a moderate pressure (50 kPa) using a silica of particle size 40–63 μm, as described by W. C.

STILL, M. KAHN and A. MITRA [J. Org. Chem., 43, 2923 (1978)].

EXAMPLE 1

3-Dimethylaminopropanethiol (1.95 g) is added to a solution of 5δ-methylenepristinamycin $I_A$ (3.6 g) in a mixture of methanol (25 cc) and chloroform (5 cc) and the solution obtained is then stirred for 20 hours at a temperature of the order of 20° C. The reaction mixture is then poured into distilled water (250 cc); the emulsion obtained is extracted 3 times with methylene chloride (250 cc in total). The organic phases are combined, dried over magnesium sulphate and filtered and the filtrate is then concentrated to dryness under reduced pressure (2.7 kPa) at 30° C. The residue obtained is purified by "flash" chromatography [eluent: chloroform/methanol (95/5 by volume)]; fractions 10 to 38 are concentrated to dryness under reduced pressure (2.7 kPa) at 30° C. The residue obtained is triturated in ethyl ether (30 cc); the crystals obtained are filtered off and then dried under reduced pressure (27 Pa) at 20° C. This gives 5δ-(3-dimethylaminopropyl)thiomethylpristinamycin $I_A$ (2.4 g) in the form of white crystals melting at 234° C. NMR spectrum:

| δ (ppm) | Shape | Assignment |
|---|---|---|
| 11.65 | s (broad) | OH |
| 8.70 | d | 6 NH |
| 8.40 | d | 1 NH |
| 7.80 | dd | 1'H$_6$ |
| 7.45 | up | 1'H$_4$ + 1'H$_5$ |
| 7.27 | up | } 6γ + 6δ + 6ε |
| 7.17 | up | |
| 7.05 | d } AB system | 4δ + 4ε |
| 6.60 | d | |
| 6.47 | d | 2 NH |
| 5.87 | ddd | 1β |
| 5.83 | d | 6α |
| 5.24 | up | 5α + 4α |
| 5.03 | ddd | 5ε$_1$ |
| 4.85 | dd | 1α |
| 4.80 | up | 2α |
| 4.53 | dd | 3α |
| 3.53 | up | 3δ$_1$ |
| 3.35 | dd } ABX system | —C$\underline{H}_2$—S—C$\underline{H}_2$— |
| 3.15 | dd | |
| 3.25 | s | 4NCH$_3$ |
| 3.25 | up | 3δ$_2$ |
| 2.90 | s | 4N(CH$_3$)$_2$ |
| 2.90 | up | 4β |
| 2.55 | t | —C$\underline{H}_2$N$\diagdown^{CH_3}_{CH_3}$ |
| 2.50 | dd | 5ε$_2$ |
| 2.40 | t | —CH$_2$SC$\underline{H}_2$— |
| 2.40 to 2.20 | up | 5δ + 5β$_1$ |
| 2.25 | s | —CH$_2$N(C$\underline{H}_3$)$_2$ |
| 2 | up | 3β$_1$ |
| 1.75 | up | —SCH$_2$C$\underline{H}_2$CH$_2$— |
| 1.8 to 1.45 | up | 2β$_1$ + 2β$_2$ + 3γ$_1$ |
| 1.30 | d | 1γ |
| 1.25 to 1.05 | up | 3γ$_2$ + 3β$_2$ |
| 0.9 | t | 2γ |

| δ (ppm) | Shape | Assignment |
|---|---|---|
| 0.60 | dd | 5β$_2$ |

A 10% aqueous solution of 5δ-(3-dimethylaminopropyl)thiomethylpristinamycin $I_A$ (product AA) is obtained with:
 product AA: 30 mg
 0.1N hydrochloric acid: q.s. 0.3 cc The 5δ-methylenepristinamycin $I_A$ can be prepared in the following manner:

Sodium cyanoborohydride (0.43 g) is added to a solution of 5δ-dimethylaminomethylenepristinamycin $I_A$ (12 g) in tetrahydrofuran (230 cc) containing trifluoroacetic acid (1.2 cc). The solution obtained is stirred for 4 hours at a temperature of the order of 20° C. and then concentrated to dryness under reduced pressure (2.7 kPa) at 30° C. The residue obtained is purified by "flash" chromatography [eluent: chloroform/methanol (95/5 by volume)]; fractions 4 to 15 are concentrated to dryness under reduced pressure (2.7 kPa) at 30° C. This gives 5δ-methylenepristinamycin $I_A$ (5.5 g) in the form of white crystals melting at 245° C.

NMR spectrum: 0.55 (dd, 1H: 5β$_2$), 2.40 (d, 1H: 5β$_1$), 3.55 (dd, 1H: 5ε$_2$), 5.25 (up, 2H: 5α+5ε$_1$), 5.30 and 6.10

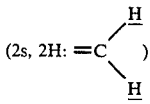

(2s, 2H: =C$\diagup^H_{\underline{H}}$)

7.85 (dd, 1H: 1'H$_6$).

The 5δ-dimethylaminomethylenepristinamycin $I_A$ can be prepared in the following manner:

Tert.-butoxybis(dimethylamino)methane (230 cc) is added to a solution of pristinamycin $I_A$ (46 g) in 1,2-dichloroethane (460 cc); the solution obtained is stirred for 18 hours at a temperature of the order of 20° C. The reaction mixture is diluted with methylene chloride (1 liter) and then washed 3 times with a 0.4% aqueous solution of ammonium chloride (3 liters in total). The organic phase is dried over magnesium sulphate and filtered and the filtrate is then concentrated to dryness under reduced pressure (2.7 kPa) at 30° C. The residue obtained is triturated with distilled water (600 cc); the mixture is filtered and the solid product is dried under reduced pressure (2.7 kPa) at 20° C. This gives crude 5δ-dimethylaminomethylenepristinamycin $I_A$ (41 g) in the form of a beige powder. This product is of sufficient quality to be used as such in the subsequent stages. However, it can be purified in the following manner:

Crude 5δ-dimethylaminomethylenepristinamycin $I_A$ (23.5 g) is purified by "flash" chromatography [eluent: chloroform/methanol (98/2 by volume)]. Fractions 16 to 25 are combined and concentrated to dryness under reduced pressure (2.7 kPa) at 30° C. This gives 5δ-dimethylaminomethylenepristinamycin $I_A$ (12 g) in the form of a beige powder melting at about 195° C.

NMR spectrum: 0.9 (t, 3H: 2γ), 1.0 (dd, 1H: 5β$_2$), 2.50 (d, 1H: 5β$_1$), 3.10 (s, 6H: —N(CH$_3$)$_2$), 3.70 (d, 1H: 5ε$_2$), 5.50 (d, 1H: 5ε$_1$), 7.40 (s, 1H: =C$\underline{H}$N(CH$_3$)$_2$), 7.75 (dd, 1H: 1'H$_6$).

EXAMPLE 2

By following a procedure analogous to that described in Example 1, but starting from 5δ-methylenevirginiamycin S (0.9 g) and 3-dimethylaminopropanethiol (0.52 g), and after purification by "flash" chromatography [eluent: chloroform/methanol (90/10 by volume)] and concentration to dryness of fractions 13 to 25 under reduced pressure (2.7 kPa) at 30° C., 5δ-(3-dimethylaminopropyl)thiomethylvirginiamycin S (0.3 g) is obtained in the form of a white powder melting at about 142° C.

NMR spectrum: 0.45 (dd, 1H: 5$\beta_2$), 1.90

(up, 2H: —SCH$_2$CH$_2$CH$_2$N$\diagup \diagdown$ )

2.40

(s, 6H: —CH$_2$—N$\diagup$CH$_3$ $\diagdown$CH$_3$ )

2.60

(up, 4H: —S—C$\underline{H}$$_2$—CH$_2$—C$\underline{H}$$_2$—N$\diagup \diagdown$ )

3.45 (d, 1H: 5$\epsilon_2$), 4.85 (up, 3H including 5$\epsilon_1$), 5.25 (dd, 1H: 5$\alpha$), 7.78 (dd, 1H: 1'H$_6$).

A 10% aqueous solution of 5δ-(3-dimethylaminopropyl)thiomethylvirginiamycin S (product AB) in the form of the hydrochloride is obtained with:
product AB: 0.1 g
hydrochloric acid: q.s. 1 cc The 5δ-methylenevirginiamycin S can be prepared in a manner analogous to that described in Example 1 for 5δ-methylenepristinamycin I$_A$, but starting from 5δ-dimethylaminomethylenevirginiamycin S (2 g) and sodium cyanoborohydride (74 mg). After purification by "flash" chromatography [eluent: chloroform/methanol (98/2 by volume)] and concentration to dryness of fractions 2 to 5 under reduced pressure (2.7 kPa) at 30° C., 5δ-methylenevirginiamycin S (1 g) is obtained in the form of a beige powder melting at about 190° C.

NMR spectrum: 0.35 (dd, 1H: 5$\beta_2$), 2.45 (dd, 1H: 5$\delta_1$), 3.55 (dd, 1H: 5$\epsilon_2$), 5.25 (dd, 1H: 5$\epsilon_1$), 5.25 (up, 1H: 5$\alpha$), 5.30 and 6.15

(2s, 2H: =C$\diagup$H $\diagdown$H )

7.75 (dd, 1H: 1'H$_6$).

The 5δ-dimethylaminomethylenevirginiamycin S can be obtained by following a procedure analogous to that described in Example 1 for 5δ-diimethylaminomethylenepristinamycin I$_A$, but starting from virginiamycin S (2 g) and bis(dimethylamino)tert.-butoxymethane (10 cc), and after purification by "flash" chromatography [eluent: chloroform/methanol (98/2 by volume)] and concentration to dryness of fractions 9 to 12 under reduced pressure (2.7 kPa) at 30° C., 5δ-dimethylaminomethylenevirginiamycin S (0.8 g) is obtained in the form of a yellow powder melting at about 175° C.

NMR spectrum: 0.9 (up, 4H: 2$\gamma$+5$\beta_2$), 3.05 (s, 6H: =CH—N(C$\underline{H}$$_3$)$_2$), 3.65 (d, 1H: 5$\epsilon_2$), 4.85 (d, 1H: 5$\epsilon_1$), 5.15 (dd, 1H: 5$\alpha$), 7.10 to 7.40

(up: aromatic protons + =C$\underline{H}$—N$\diagup \diagdown$ )

7.70 (dd, 1H: 1'H$_6$).

EXAMPLE 3

By following a procedure analogous to that described in Example 1, but starting from 5δ-methylenepristinamycin I$_A$ (6 g) and 2-(4-methylpiperazin-1-yl)ethanethiol (4 cc), and after purification by "flash" chromatography [eluent: chloroform/methanol (97/3 by volume)] and concentration to dryness of fractions 8 to 20 under reduced pressure (2.7 kPa) at 30° C., 5δ-[2-(4-methylpiperazin-1-yl)ethyl]thiomethylpristinamycin I$_A$ (2.6 g) is obtained in the form of white crystals melting at 216° C.

NMR spectrum: 0.60 (dd, 1H: 5$\beta_2$), 2.27 (s, 3H: >N—CH$_3$), 2.40 to 2.80

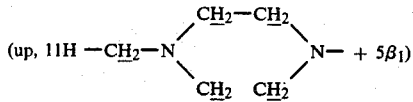

5.05 (dd, 1H: 5$\epsilon_1$), 5.27 (up, 2H: 5$\alpha$+4$\alpha$), 7.85 (mt, 1H×0.8: 1'H$_6$ 1st isomer), 7.95 (mt, 1H×0.2: 1'H$_6$ 2nd isomer).

A 5% aqueous solution of 5δ-[2-(4-methylpiperazin-1-yl)ethyl]thiomethylpristinamycin I$_A$ (product AC) in the form of the hydrochloride is obtained with:
product AC: 0.1 g
0.1N hydrochloric acid: 0.96 cc
distilled water: q.s. 2 cc The 2-(4-methylpiperazin-1-yl)ethanethiol can be prepared according to the method described by D. D. REYNOLDS et al., J. Org. Chem. 26, 5125 (1961).

EXAMPLE 4

By following a procedure analogous to that described in Example 1, but starting from 5δ-methylenepristinamycin I$_A$ (2 g) and 3-(4-methylpiperazin-1-yl)propanethiol (3 cc), and after purification by "flash" chromatography [eluent: chloroform/methanol (90/10 by volume)] and concentration to dryness of fractions 10 to 25 under reduced pressure (2.7 kPa) at 30° C., 5δ-[3-(4-methylpiperazin-1-yl)propyl]thiomethylpristinamycin I$_A$ (1.9 g) is obtained in the form of a white powder melting at about 156° C.

NMR spectrum: 0.65 (dd, 1H: 5$\beta_2$), 2.30 (s, 3H: >N—CH$_3$), 2.50

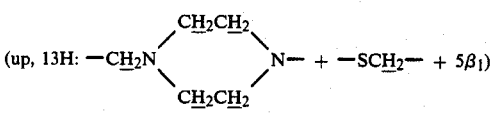

5.27 (up, 2H: 5α+4α), 7.85 (dd, 1H×0.8: 1′H₆ 1st isomer), 7.95 (dd, 1H×0.2: 1′H₆ 2nd isomer).

A 10% aqueous solution of 5δ-[3-(4-methylpiperazin-1-yl)propyl]thiomethylpristinamycin I$_A$ (product AD) in the form of the hydrochloride is obtained with:
product AD: 0.1 g
0.5N hydrochloric acid: 0.38 cc
distilled water: q.s. 1 cc The 3-(4-methylpiperazin-1-yl)propanethiol can be prepared as below in Example 41.

EXAMPLE 5

By following a procedure analogous to that described in Example 1, but starting from 5δ-methylenepristinamycin I$_A$ (4 g) and 1,3-bis(dimethylamino)propane-2-thiol (4 cc), and after purification by "flash" chromatography [eluent: chloroform/methanol (95/5 by volume)] and concentration to dryness of fractions 20 to 60 under reduced pressure (2.7 kPa) at 30° C., 5δ-[1,3-bis(dimethylamino)prop-2-yl]thiomethylpristinamycin I$_A$ (0.59 g) is obtained in the form of a white powder melting at about 170° C.

NMR spectrum: 0.63 (dd, 1H: 5β₂), 2.40 (s, 6H: —N(CH₃)₂), 2.50

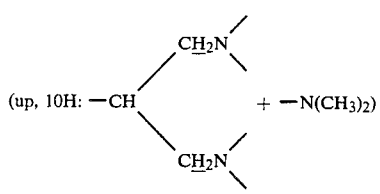

4.97 (s, 1H: 5ε₁), 5.30 (up, 2H: 5α+4α), 7.85 (mt, 1H×0.85: 1′H₆ 1st isomer), 7.95 (mt, 1H×0.15: 1′H₆ 2nd isomer).

A 7.5% aqueous solution of 5δ-[1,3-bis(dimethylamino)prop-2-yl]thiomethylpristinamycin I$_A$ (product AE) in the form of the hydrochloride is obtained with:
product AE: 0.03 g
0.1N hydrochloric acid: 0.3 cc
distilled water: q.s. 0.4 cc The 1,3-bis(dimethylamino)propane-2-thiol can be prepared as below in Example 39.

EXAMPLE 6

By following a procedure analogous to that described in Example 1, but starting from 5δ-methylenepristinamycin I$_A$ (3 g) and 1-methyl-4-mercaptopiperidine (0.97 g), and after purification by "flash" chromatography [eluent: chloroform/methanol (95/5 by volume)] and concentration to dryness of fractions 10 to 16 under reduced pressure (2.7 kPa) at 30° C., 5δ-(1-methyl-piperidin-4-yl)thiomethylpristinamycin I$_A$ (1.1 g) is obtained in the form of a white powder melting at 260° C.

NMR spectrum: 0.6 (dd, 1H: 5β₂), 2

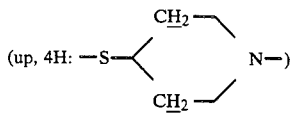

2.20

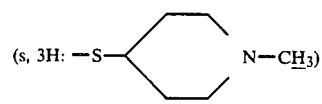

2.35 (up, 1H: 5β₁), 2.90

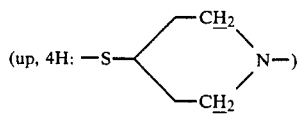

5.30 (up, 2H: 5α+4α) 7.85 (dd, 1H: 1′H₆).

A 5% aqueous solution of 5δ-(1-methylpiperidin-4-yl)thiomethylpristinamycin I$_A$ (product AF) in the form of the hydrochloride is obtained with:
product AF: 0.03 g
0.1N hydrochloric acid: 0.3 cc
distilled water: q.s. 0.6 cc The 1-methyl-4-mercaptopiperidine can be prepared according to the method described by H. BARRER and R. E. LYLE, J. Org. Chem. 27, 641 (1962).

EXAMPLE 7

By following the procedure of Example 1, but starting from 5δ-methylenepristinamycin I$_A$ (2 g) and 2-diethylaminoethanethiol (0.66 g), and after purification by "flash" chromatography [eluent: chloroform/methanol (95/5 by volume)] and concentration to dryness of fractions 9 to 18 under reduced pressure (2.7 kPa) at 30° C., 5δ-(2-diethylaminoethyl)thiomethylpristinamycin I$_A$ (0.8 g) is obtained in the form of a beige powder melting at 230° C.

NMR spectrum: 0.65 (dd, 1H: 5β₂), 2.38 (d, 1H: 5β₁), 2.3 to 2.8

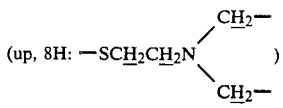

3.15 (dd, 1H: —CH₂S—), 3.35 (dd, 1H: —CH₂S—), 5.01 (dd, 1H: 5ε₁), 7.81 (dd, 1H×0.9: 1′H₆ 1st isomer), 7.90 (dd, 1H×0.1: 1′H₆ 2nd isomer).

A 5% aqueous solution of 5δ-(2-diethylaminoethyl)-thiomethylpristinamycin I$_A$ (product AF₁) in the form of the hydrochloride is obtained with:
product AF₁: 30 mg
0.1N hydrochloric acid: 0.29 cc
distilled water: q.s. 0.6 cc

EXAMPLE 8

By following a procedure analogous to that described in Example 1, but starting from 5δ-methylenepristinamycin I$_A$ (4.36 g) and 1-diethylaminopropane-2-thiol (2.2 g), and after purification by "flash" chromatography [eluent: chloroform/methanol (96/4 by volume)] and concentration to dryness of fractions 10 to 25 under reduced pressure (2.7 kPa) at 30° C., 5δ-(1-diethylaminoprop-2-yl)thiomethylpristinamycin I$_A$ (1 g) is obtained in the form of a beige powder melting at about 190° C.

NMR spectrum: 0.64 (dd, 1H: 5β₂), 1 to 1.2 (up, CH₃—CH< and —CH₂—CH₃), 2.37 (d, 1H: 5β₁), 2.3 to 2.7

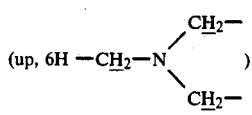

3.15 (dd, 1H: —CH$_2$—S), 3.35 (dd, 1H: —CH$_2$—S), 5.02 (dd, 1H:5ε$_1$) 7.85 (up, 1H×0.9: 1'H$_6$ 1st isomer), 7.93 (up, 1H×0.1: 1'H$_6$ 2nd isomer).

A 4% solution of 5δ-(1-diethylaminoprop-2-yl)thiomethylpristinamycin I$_A$ (product AF$_2$) in the form of the hydrochloride is obtained with:
  product AF$_2$: 30 mg
  0.1N hydrochloric acid: 0.29 cc
  distilled water: q.s. 0.75 cc The 1-diethylaminopropane-2-thiol can be prepared according to the method described by R. T. WRAGG, J. Chem. Soc. (C), 2087 (1969).

EXAMPLE 9

By following a procedure analogous to that described in Example 1, but starting from 5δ-methylenepristinamycin I$_A$ (3.2 g) and N,N-bis(2-mercaptoethyl)-N-methylamine (2.8 g), and after purification by "flash" chromatography [eluent: methylene chloride/methanol (98/2 by volume)] and concentration to dryness of fractions 7 to 20 under reduced pressure (2.7 kPa) at 30° C., 5δ-{2-[N-(2-mercaptoethyl)-N-methylamino]ethyl}thiomethylpristinamycin I$_A$ (1 g) is obtained in the form of a white powder melting at about 100° C.

NMR spectrum: 0.61 (dd, 1H: 5β$_2$), 2.29 (s, 3H: >N—CH$_3$), 2.38 (d, 1H: 5β$_1$), 2.3 to 2.7 (up, 8H: —SCH$_2$CH$_2$N—CH$_2$CH$_2$SH), 3.15 (dd, 1H: —CH$_2$S—), 3.35 (dd, 1H: —CH$_2$S—), 5.03 (dd, 1H: 5ε$_1$), 7.83 (dd, 1H×0.9: 1'H$_6$ 1st isomer), 7.93 (dd, 1H×0.1: 1'H$_6$ 2nd isomer).

A 1% aqueous solution of 5δ-{2-[N-(2-mercaptoethyl)-N-methylamino]ethyl}thiomethylpristinamycin I$_A$ (product AF$_3$) in the form of the hydrochloride is obtained with:
  product AF$_3$: 20 mg
  0.1N hydrochloric acid: 0.38 cc
  distilled water: q.s. 2 cc

EXAMPLE 10

By following a procedure analogous to that described in Example 1, but starting from 5δ-methylenepristinamycin I$_A$ (7.7 g) and 1,4-bis(2-mercaptoethyl)piperazine (9 g), and after purification by "flash" chromatography [eluent: methylene chloride/methanol (95/5 by volume)] and concentration to dryness of fractions 12 to 40 under reduced pressure (2.7 kPa) at 30° C., 5δ-{2-[4-(2-mercaptoethyl)piperazinyl]ethyl}thiomethylpristinamycin I$_A$ (4.2 g) is obtained in the form of a yellow powder melting at about 165° C.

NMR spectrum: 0.61 (dd, 1H: 5β$_2$), 2.37 (dd, 1H: 5β$_1$), 2.30 to 2.80

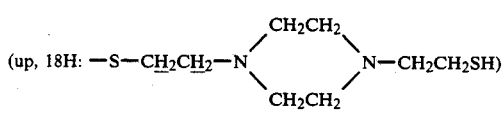

3.17 (dd, 1H: —CH$_2$—S—), 3.35 (dd, 1H: —CH$_2$—S—), 5.03 (dd, 1H: 5ε$_1$), 7.85 (up, 1H×0.85: 1'H$_6$ 1st isomer), 7.95 (up, 1H×0.15: 1'H$_6$ 2nd isomer).

A 2% aqueous solution of 5δ-{2-[4-(2-mercaptoethyl)piperazinyl]ethyl}thiomethylpristinamycin I$_A$ (product AF$_4$) in the form of the hydrochloride is obtained with:
  product AF$_4$: 20 mg
  0.1N hydrochloric acid: 0.36 cc
  distilled water: q.s. 1 cc The 1,4-bis(2-mercaptoethyl)piperazine can be prepared according to the method described by D. D. REYNOLDS, M. K. MASSAD, D. L. FIELDS and D. L. JOHNSON, J. Org. Chem. 26, 5111 (1961).

EXAMPLE 11

2-Dimethylaminoethylamine (5.3 g) is added dropwise to a solution of 5δ-dimethylaminomethylenepristinamycin I$_A$ (5.5 g) in acetic acid (60 cc) so as not to exceed 25° C. The solution obtained is stirred for 20 hours at a temperature of the order of 20° C. and is then poured slowly into a saturated aqueous solution of sodium bicarbonate; the mixture obtained is extracted twice with methylene chloride (750 cc in total). The organic phases are combined, dried over magnesium sulphate and filtered and the filtrate is concentrated to dryness under reduced pressure (2.7 kPa) at 30° C. The residue is purified by "flash" chromatography [eluent: chloroform/methanol (90/10 by volume)]; fractions 10 to 12 are concentrated to dryness under reduced pressure (2.7 kPa) at 30° C. This give 5δ-(2-dimethylaminoethyl)aminomethylenepristinamycin I$_A$ (3 g) in the form of a beige powder melting at about 180° C.

NMR spectrum: 0.90 (mt; 4H: 2γ+5β$_2$) 2.25 (mt; 6H: —N(CH$_3$)$_2$), 2.50 (mt; 3H: —CH$_2$N<+5β$_1$), 3.25 (mt; 2H: —N—CH$_2$—), 3.50 (mt; 2H: 5ε$_2$+3δ$_1$), 4.90 (mt; 1H: 5ε$_1$), between 7.15 and 7.4

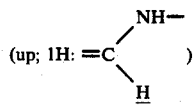

9.90 (mt; 1H (exchangeable with D$_2$O): —NH—).

A 1% aqueous solution of 5δ-(2-dimethylaminoethyl)aminomethylenepristinamycin I$_A$ (product AG) is obtained with:
  product AG: 0.1 g
  distilled water: q.s. 10 cc

EXAMPLE 12

By following a procedure analogous to that described in Example 11, but starting from 5δ-dimethylaminomethylenepristinamycin I$_A$ (1.84 g) and 2-diethylaminoethylamine (2.8 cc), and after purification by "flash" chromatography [eluent: chloroform/methanol (96/4 by volume)] and concentration to dryness of fractions 9 to 13 under reduced pressure (2.7 kPa) at 30° C., 5δ-(2-diethylaminoethyl)aminomethylenepristinamycin I$_A$ (1 g) is obtained in the form of a yellow powder melting at about 150° C.

NMR spectrum: 0.9 (mt; 4H: 2γ+5β$_2$), 1.1 (mt; 6H: —N(CH$_2$—CH$_3$)$_2$), 2.45 (d; 1H: 5β$_1$), 3.1 to 3.4

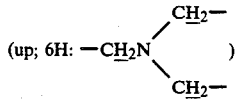

3.50 (mt; 2H: 5ε$_2$+3δ$_1$), 4.90 (up; 1H: 5ε$_1$), 9.9 (up; 1H (exchangeable): =CH—NH—).

A 5% aqueous solution of 5δ-(2-diethylaminoethyl)aminomethylenepristinamycin I$_A$ (product AH) in the form of the hydrochloride is obtained with:
product AH: 0.1 g
0.1N hydrochloric acid: 1 cc
distilled water: q.s. 2 cc

EXAMPLE 13

By following a procedure analogous to that described in Example 11, but starting from 5δ-dimethylaminomethylenepristinamycin I$_A$ (2.76 g) and N-methylethylenediamine (2.22 g), and after purification by "flash" chromatography [eluent: chloroform/methanol (95/5 by volume)] and concentration to dryness of fractions 16 to 20 under reduced pressure (2.7 kPa) at 30° C., 5δ-(2-methylaminoethyl)aminomethylenepristinamycin I$_A$ (1.3 g) is obtained in the form of a yellow powder melting at 174° C.

NMR spectrum: 0.90 (up; 4H: 5β$_2$), 2.50 (up; 1H: 5β$_1$), 2.7–3.6 (up; 4H: —NH—(CH$_2$)$_2$NH—), 3.0 (under unresolved peaks, s; 3H: —NHCH$_3$), 7.15–7.40 (up; 1H: =CHNH—), 9.90 (up; 1H: =CH—NHCH$_3$).

A 1% aqueous solution of 5δ-(2-methylaminoethyl)aminomethylenepristinamycin I$_A$ (product AI) in the form of the hydrochloride is obtained with:
product AI: 0.03 g
0.1N hydrochloric acid: 0.31 cc
distilled water: q.s. 3 cc

EXAMPLE 14

By following a procedure analogous to that described in Example 11, but starting from 5δ-dimethylaminomethylenepristinamycin I$_A$ (1.84 g) and 3-dimethylaminopropylamine (2.5 cc), and after purification by "flash" chromatography [eluent: chloroform/methanol (90/10 by volume)] and concentration to dryness of fractions 12 to 15 under reduced pressure (2.7 kPa) at 155° C., 5δ-(3-dimethylaminopropyl)aminomethylenepristinamycin I$_A$ (0.7 g) is obtained in the form of a yellow powder melting at about 155° C.

NMR spectrum: 0.80 to 1.05 (mt; 4H: 2γ+5β$_2$), 1.80 (mt; 2H: —CH$_2$—CH$_2$—CH$_2$—), 2.35 (s; 6H×0.85: —N(CH$_3$)$_2$ 1st isomer), 2.40 (s; 6H×0.15: —N(CH$_3$)$_2$ 2nd isomer), 2.40 to 2.60 (mt; 3H: 5β$_1$+—CH$_2$—N<), 3.30 (mt; 2H: —NH—CH$_2$—), 3.50 (mt; 2H: 3δ$_1$+5ε$_2$), 4.90 (mt; 1H: 5ε$_1$), 9.65 (up; 1H×0.15: =CH—NH— 2nd isomer), 9.90 (up; 1H×0.85: =CH—NH— 1st isomer).

A 6.6% solution of 5δ-(3-dimethylaminopropyl)aminomethylenepristinamycin I$_A$ (product AJ) in the form of the hydrochloride is obtained with:
product AJ: 0.1 g
0.2N hydrochloric acid: 0.51 cc
distilled water: q.s. 1.5 cc

EXAMPLE 15

By following a procedure analogous to that described in Example 11, but starting from 5δ-dimethylaminomethylenepristinamycin I$_A$ (2.76 g) and 1-dimethylaminoprop-2-ylamine (3.06 g), and after purification by "flash" chromatography [eluent: chloroform/methanol (99/1 by volume)] and concentration to dryness of fractions 11 to 22 under reduced pressure (2.7 kPa) at 30° C., 5δ-(3-dimethylaminoprop-2-yl)aminomethylenepristinamycin I$_A$ (1.0 g) is obtained in the form of a yellow powder melting at about 160° C.

NMR spectrum: 1.05

(d; 3H: —CH—CH$_3$)

2.30 (s; 6H: —CH$_2$—N(CH$_3$)$_2$), 2.45 (d; 1H: 5β$_1$), 2.80

(up; 1H: —CHCH$_3$)

3.30 (under unresolved peaks: —NH—CH$_2$—), 3.45 (up; 2H: 5ε$_2$+3δ$_1$), 4.90 (up; 1H: 5ε$_1$), 7.15–7.40 (up; 1H: =CHNH—), 9.90 (up; 1H: =CH—NH—).

A 1% aqueous solution of 5δ-(3-dimethylaminoprop-2-yl)aminomethylenepristinamycin I$_A$ (product AK) in the form of the hydrochloride is obtained with:
product AK: 20 mg
0.1N hydrochloric acid: 0.2 cc
distilled water: q.s. 2 cc

EXAMPLE 16

By following a procedure analogous to that described in Example 11, but starting from 5δ-dimethylaminomethylenepristinamycin I$_A$ (2.76 g) and 2-dimethylaminopropylamine (1.53 g), and after purification by "flash" chromatography [eluent: chloroform/methanol (95/5 by volume)] and concentration to dryness of fractions 10 to 14 under reduced pressure (2.7 kPa) at 30° C., 5δ-(2-dimethylaminopropyl)aminomethylenepristinamycin I$_A$ (0.85 g) is obtained in the form of an orange powder melting at about 175° C.

NMR spectrum: 0.90 (up; 4H: 2γ+5β$_2$), 1.05 (d; 3H: >CH—CH$_3$), 2.30 (s; 6H: —CH(CH$_3$)N(CH$_3$)$_2$), 2.45 (d; 1H: 5β$_1$), 2.80

(up; 1H: —CHCH$_3$)

3.30 (under unresolved peaks, 2H: —NH—CH$_2$—), 3.45 (up; 2H: 5ε$_2$+3δ$_1$), 4.90 (up; 1H: 5ε$_1$), 7.15–7.40 (up; 1H: =CHNH—), 9.90 (up; 1H: =CH—NH—).

A 10% aqueous solution of 5δ-(2-dimethylaminopropyl)aminomethylenepristinamycin I$_A$ (product AL) in the form of the hydrochloride is obtained with:
product AL: 0.03 g
0.1N hydrochloric acid: 0.31 cc

EXAMPLE 17

By following a procedure analogous to that described in Example 11, but starting from 5δ-dimethylaminomethylenepristinamycin I$_A$ (1.84 g) and 2-amino-5-diethylaminopentane (3.16 g), and after purification by "flash" chromatography [eluent: chloroform/methanol (90/10 by volume)] and concentration to dryness of fractions 15 to 27 under reduced pressure (2.7 kPa) at 30° C., 5δ-(5-diethylaminopent-2-yl)aminomethylenepristinamycin I$_A$ (0.9 g) is obtained in the form of a beige powder melting at about 160° C.

NMR spectrum: 1.00 (dd; 1H: 5β$_2$), 1.25 (mt; 6H: —N(CH$_2$CH$_3$)$_2$), 2.45 (d; 1H: 5β$_1$), 2.7–3.0

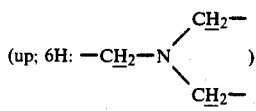

3.45 (dd; 1H: 5ε₂), 7.30 (under the aromatic protons: =C$\underline{H}$—NH—), 7.85 (dd; 1H: 1'H₆), (up broad; 1H: —N$\underline{H}$—C$\underline{H}$—)

A 1% aqueous solution of 5δ-(5-diethylaminopent-2-yl)aminomethylenepristinamycin I$_A$ (product AM) in the form of the hydrochloride is obtained with:
product AM: 0.02 g
0.1N hydrochloric acid: 0.2 cc
distilled water: q.s. 2 cc

EXAMPLE 18

By following a procedure analogous to that described in Example 11, but starting from 5δ-dimethylaminomethylenepristinamycin I$_A$ (1.84 g) and N-(2-aminoethyl)-pyrrolidine (2.28 g), and after purification by "flash" chromatography [eluent: chloroform/methanol (98/2 by volume)] and concentration to dryness of fractions 15 to 24 under reduced pressure (2.7 kPa) at 30° C., 5δ-(2-pyrrolidinoethyl)aminomethylenepristinamycin I$_A$ (0.95 g) is obtained in the form of a yellow powder melting at 183° C.

NMR spectrum: 0.90 (mt; 4H: 2γ+5β₂), 1.80

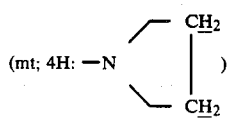

2.70

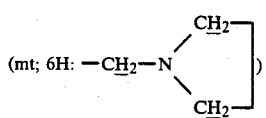

3.45 (up; 4H: —NH—CH₂—+5ε₂+3δ₁), 4.90 (up; 1H: 5ε₁), 7.2–7.4 (up: Ar+1'$\underline{H}$₄+1'H₅+=C$\underline{H}$—), 9.90 (mt; 1H: =CHNH$\underline{C}$H₂—).

A 1% solution of 5δ-(2-pyrrolidinoethyl)aminomethylenepristinamycin I$_A$ (product AN) in the form of the hydrochloride is obtained with:
product AN: 0.02 g
0.1N hydrochloric acid: 0.2 cc
distilled water: q.s. 2 cc

EXAMPLE 19

By following a procedure analogous to that described in Example 11, but starting from 5δ-dimethylaminomethylenepristinamycin I$_A$ (2.76 g) and N-(3-aminopropyl)pyrrolidine (1.92 g), and after purification by "flash" chromatography [eluent: chloroform/methanol (95/5 by volume)] and concentration to dryness of fractions 10 to 15 under reduced pressure (2.7 kPa) at 30° C., 5δ-(3-pyrrolidinopropyl)aminomethylenepristinamycin I$_A$ (1.25 g) is obtained in the form of a yellow powder melting at 170° C.

NMR spectrum: 0.95 (up; 1H: 5β₂), 1.95

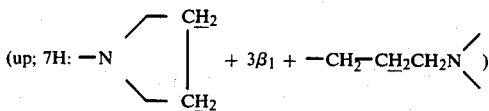

2.45 (d broad; 1H: 5β₁), 2.80

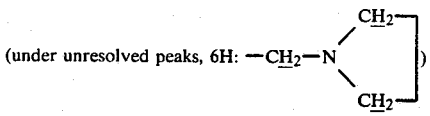

3.30 (mt; 2H: —NH—CH₂—), 3.50 (mt; 2H: 3δ₁+5ε₂), 4.90 (up; 1H: 5ε₁), 7.15–7.40 (up; 1H: =CHNH—), 9.90 (mt; 1H: =CH—N$\underline{H}$—).

A 1% aqueous solution of 5δ-(3-pyrrolidinopropyl)aminomethylenepristinamycin I$_A$ (product AO) is obtained with:
product AO: 0.03 g
distilled water: 3 cc

EXAMPLE 20

By following a procedure analogous to that described in Example 11, but starting from 5δ-dimethylaminomethylenepristinamycin I$_A$ (2.76 g) and N-(2-aminoethyl)-piperidine (3.85 g), and after purification by "flash" chromatography [eluent: chloroform/methanol (99/1 by volume)] and concentration to dryness of fractions 13 to 17 under reduced pressure (2.7 kPa) at 30° C., 5δ-(2-piperidinoethyl)aminomethylenepristinamycin I$_A$ (1.5 g) is obtained in the form of a yellow powder melting at about 162° C.

NMR spectrum: 0.90 (up; 4H: 2γ+5β₂), 1.60

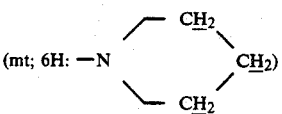

2.40

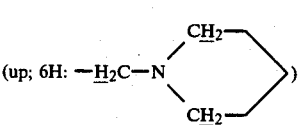

2.7–3.5 (up under unresolved peaks; 2H: —NH—CH₂—), 3.45 (mt; 2H: 3δ₁+5ε₂), 4.90 (mt; 1H: 5ε₁), 7.15–7.40 (up; 1H: =C$\underline{H}$NH—), 9.90 (mt; 1H: =CH—N$\underline{H}$—).

A 1% aqueous solution of 5δ-(2-piperidinoethyl)aminomethylenepristinamycin I$_A$ (product AP) in the form of the hydrochloride is obtained with:
product AP: 0.02 g
0.1N hydrochloric acid: 0.2 cc
distilled water: q.s. 2 cc

EXAMPLE 21

By following a procedure analogous to that described in Example 11, but starting from N-(2-aminoethyl)morpholine (2.6 g) and 5δ-dimethylaminomethylenepristinamycin I$_A$ (1.84 g), and after purification by "flash" chromatography [eluent: chloroform/methanol (95/5 by volume)] and concentration to dryness of fractions 21 to 30 under reduced pressure (2.7 kPa) at 30° C., 5δ-(2-morpholinoethyl)aminomethylenepristinamycin I$_A$ (0.8 g) is obtained in the form of a beige powder melting at about 172° C.

NMR spectrum: 0.95 (up; 1H: 5β$_2$), 2.50

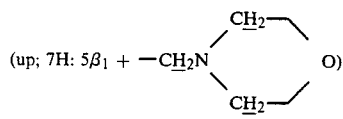

3.30 (up; 2H: —NH—CH$_2$—), 3.50 (up; 2H: 5ε$_2$+3δ$_1$), 3.70

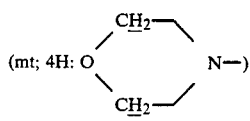

4.90 (up; 1H: 5ε$_1$), 7.2–7.4 (up; 1H: =CH—), 9.90 (mt; 1H: =CH—NH—CH$_2$—).

A 1% aqueous solution of 5δ-(2-morpholinoethyl)aminomethylenepristinamycin I$_A$ (product AQ) in the form of the hydrochloride is obtained with:
 product AQ: 0.02 g
 0.1N hydrochloric acid: 0.2 cc
 distilled water: q.s. 2 cc

EXAMPLE 22

By following a procedure analogous to that described in Example 11, but starting from 5δ-dimethylaminomethylenepristinamycin I$_A$ (2.76 g) and 2-aminomethyl-1-ethylpyrrolidine (3.66 g), and after purification by "flash" chromatography [eluent: chloroform/methanol (99/1 by volume)] and concentration to dryness of fractions 10 to 14 under reduced pressure (2.7 kPa) at 30° C., 5δ-(1-ethylpyrrolidin-2-yl)methylaminomethylenepristinamycin I$_A$ (1.3 g) is obtained in the form of a beige powder melting at about 160° C.

NMR spectrum: 1.10 (t; 3H: —CH$_2$—CH$_3$), 1.60

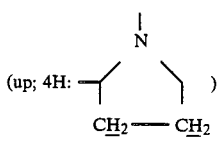

1.95 (up; 1H: =CH—NH—), 2.8–3.6 (up; 4H: —CH$_2$N< +—CH$_2$NH—), 7.15–7.40 (up; 1H: =CHNH—).

A 1% aqueous solution of 5δ-(1-ethylpyrrolidin-2-yl)methylaminomethylenepristinamycin I$_A$ (product AR) in the form of the hydrochloride is obtained with:
 product AR: 0.02 g
 0.1N hydrochloric acid: 0.2 cc
 distilled water: q.s. 2 cc

EXAMPLE 23

By following a procedure analogous to that described in Example 11, but starting from 5δ-dimethylaminomethylenepristinamycin I$_A$ (2.77 g) and 3-amino-1-methylpiperidine (3.4 g), and after purification by "flash" chromatography [eluent: chloroform/methanol (95/5 by volume)] and concentration to dryness of fractions 7 to 16 under reduced pressure (2.7 kPa) at 30° C., 5δ-(1-methylpiperidin-3-yl)aminomethylenepristinamycin I$_A$ (0.8 g) is obtained in the form of a beige powder melting at 177° C.

NMR spectrum: 0.90 (mt; 4H: 2γ+5β$_2$), 1.5–2.10

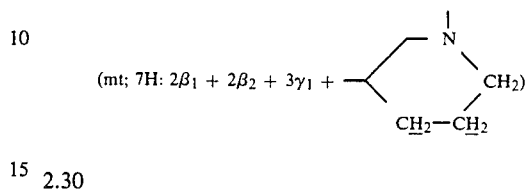

2.30

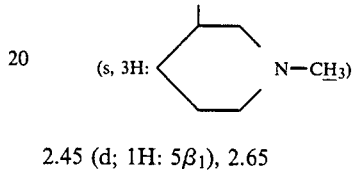

2.45 (d; 1H: 5β$_1$), 2.65

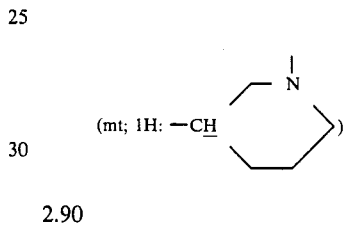

2.90

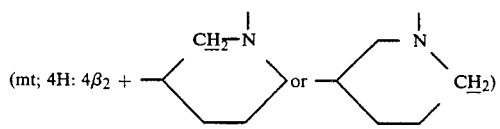

3.20

(mt; 7H: —NCH$_3$ in the 4-position + 3δ$_2$ + 4β$_1$ +

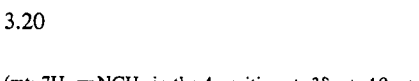

7.15–7.40 (up; 1H: =CHNH—), 7.80 (mt; 1H: 1'H$_6$), 9.90 (mt; 1H: =CH—NH—), 11.60 (s broad; 1H: OH).

A 1% aqueous solution of 5δ-(1-methylpiperidin-3-yl)aminomethylenepristinamycin I$_A$ (product AS) in the form of the hydrochloride is obtained with:
 product AS: 0.02 g
 0.1N hydrochloric acid: 0.2 cc
 distilled water: q.s. 2 cc The 3-amino-1-methylpiperidine can be prepared according to the method described by L. M. WERBEL, A. CURRY, E. F. ELSLAGER and C. HESS, J. Heterocyclic Chem. 10, 363 (1973).

EXAMPLE 24

By following a procedure analogous to that described in Example 11, but starting from 5δ-dimethylaminomethylenepristinamycin I$_A$ (13.8 g) and 4-amino-1-methylpiperidine (3.4 g), and after purification by "flash" chromatography [eluent: chloroform/methanol (92.5/7.5 by volume)] and concentration to dryness of fractions 15 to 20 under reduced pressure (2.7 kPa) at 30° C., 5δ-(1-methylpiperidin-4-yl)aminomethylenepristinamycin $I_A$ (4.0 g) is obtained in the form of a yellow powder melting at 208° C.

NMR spectrum: 0.40 (up; 4H: $2\gamma+2\beta_2$) 2.0

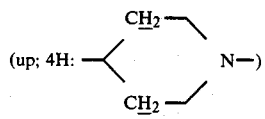

2.35 (s; 3H: <N—CH₃), 2.45 (d; 1H: $5\beta_1$), 2.90

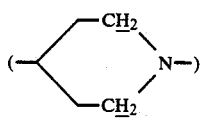

3.20

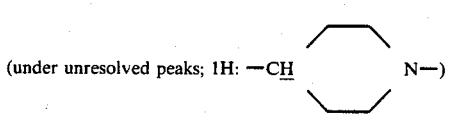

3.50 (d; 1H: $5\epsilon_2$), 4.85 (under unresolved peaks; 1H: $5\epsilon_1$), 6.65 (d; 1H: =CHNH—), 9.70 (dd; 1H×0.25: =CH—NH— 1st isomer), 10.03 (dd; 1H×0.85: =CH—NH— 2nd isomer).

A 10% aqueous solution of 5δ-(1-methylpiperidin-4-yl)aminomethylenepristinamycin $I_A$ (product AT) in the form of the hydrochloride is obtained with:
product AT: 0.03 g
0.1N hydrochloric acid: 0.3 cc
distilled water: q.s. 0.3 cc The 4-amino-1-methylpiperidine can be prepared by the method described by E. F. ELSLAGER, L. M. WERBEL, A. CURRY, N. HEADEN and J. JOHNSON, J. Med. Chem. 17, 99 (1974).

EXAMPLE 25

By following a procedure analogous to that described in Example 11, but starting from 5δ-dimethylaminomethylenevirginiamycin S (0.8 g) and 4-amino-1-methylpiperidine (1.02 g), and after purification by "flash" chromatography [eluent: chloroform/methanol (90/10 by volume)] and concentration to dryness of fractions 3 to 7 under reduced pressure (2.7 kPa) at 30° C., 5δ-(1-methylpiperidin-4-yl)aminomethylenevirginiamycin S (0.3 g) is obtained in the form of a beige powder melting at about 195° C.

NMR spectrum: 0.9 (up; 4H: $2\gamma+5\beta_2$), 2.30

2.80 to 3.30

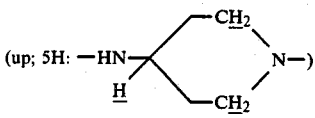

3.55 (dd; 1H: $5\epsilon_2$), 4.90 (up; 1H: $5\epsilon_1$), 7.10 to 7.40 (up; aromatic protons+=CH—NH—), 7.70 (dd; 1H: 1'H₆), 10.1 (up; 1H: =CH—NH—).

A 5% aqueous solution of 5δ-(1-methylpiperidin-4-yl)aminomethylenevirginiamycin S (product AU) in the form of the hydrochloride is obtained with:
product AU: 0.1 g
0.1N hydrochloric acid: 1.05 cc
distilled water: q.s. 2 cc

EXAMPLE 26

By following a procedure analogous to that described in Example 11, but starting from 5δ-dimethylaminomethylenepristinamycin $I_A$ (2.76 g) and 1-(2-aminoethyl)-4-methylpiperazine (2.15 g), and after purification by "flash" chromatography [eluent: chloroform/methanol (95/5 by volume)] and concentration to dryness of fractions 10 to 16 under reduced pressure (2.7 kPa) at 30° C., 5δ-[2-(4-methylpiperazin-1-yl)ethyl]aminomethylenepristinamycin $I_A$ (0.9 g) is obtained in the form of a yellow powder melting at 150° C.

NMR spectrum: 1.00 (up; 1H: $5\beta_2$), 2.30 (s; 3H: >N—CH₃), 2.50 (up; 9H: —CH₂—piperazine+$5\beta_1$), 2.90 (under unresolved peaks: —CH₂—CH₂—N<), 3.30 (up; 2H: —NH—CH₂—), 3.50 (up; 2H: $5\epsilon_2+3\delta_1$), 4.90 (up; 1H: $5\epsilon_1$), 7.15–7.40 (up; 1H: =CHNH—), 9.90 (up; 1H: =CH—NH—).

A 10% aqueous solution of 5δ-[2-(4-methylpiperazin-1-yl)ethyl]aminomethylenepristinamycin $I_A$ (product AV) in the form of the hydrochloride is obtained with:
product AV: 15 mg
0.1N hydrochloric acid: 0.15 cc The 1-(2-aminoethyl)-4-methylpiperazine can be prepared in the following manner:

N-Methylpiperazine (9.75 g) is added to a solution of 2-bromoethylamine hydrobromide (10.0 g) in absolute ethanol (60 cc). The solution obtained is stirred for 16 hours at a temperature of the order of 20° C. and the ethanol is then removed under reduced pressure (2.7 kPa) at 30° C. The oily residue is taken up with chloroform (50 cc); the mixture obtained is stirred with a 10N aqueous solution of sodium hydroxide (20 cc). The aqueous phase is extracted 3 times with chloroform (150 cc in total). The organic phases are combined, dried over sodium sulphate and filtered and the filtrate is concentrated to dryness under reduced pressure (2.7 kPa) at 30° C. The residue is distilled under reduced pressure (2.7 kPa); this gives 1-(2-aminoethyl)-4-methylpiperazine (4.5 g) in the form of a yellow oil [b.p. (2.7 kPa)=118°–119° C.].

EXAMPLE 27

By following a procedure analogous to that described in Example 11, but starting from 5δ-dimethylaminomethylenepristinamycin $I_A$ (4.0 g) and histamine (0.55 g), and after purification by "flash" chromatography [eluent: chloroform/methanol (95/5 by volume)] and concentration to dryness of fractions 25 to 50 under reduced pressure (2.7 kPa) at 30° C., 5δ-[2-(imidazol-4-yl)ethyl]aminomethylenepristinamycin $I_A$ (2.04 g) is obtained in the form of a yellow powder melting at 138° C.

NMR spectrum: 0.90 (up; 4H: 2γ+5β$_2$), 2.40 (d broad; 1H: 5β$_1$), 2.90 (under unresolved peaks, up; 1H: 5ε$_1$), 3.50 (d; 4H: 5ε$_2$+3δ$_1$+—NH—CH$_2$—), 4.80 (under unresolved peaks, 1H: 5ε$_1$), 6.65 (up; 2H: H$_5$+ >NH histamine), 7.50 (s; 1H, H in the 2-position of the histamine), between 7.15 and 7.40 (up; 1H: =CHNH—), 9.65 (up; 1H×0.15: =CH—NH— 2nd isomer), 9.95 (up; 1H×0.85: =CH—NH— 1st isomer).

A 10% aqueous solution of 5δ-[2-(imidazol-4-yl)ethylaminomethylene]pristinamycin I$_A$ (product AW) in the form of the hydrochloride is obtained with:
  product AW: 0.1 g
  0.1N hydrochloric acid: q.s. 1 cc

EXAMPLE 28

2-Dimethylaminoethanethiol (2.1 g) is added to a solution of 5δ-dimethylaminomethylenepristinamycin I$_A$ (1.84 g) in acetic acid (40 cc). The solution obtained is stirred for 20 hours at a temperature of the order of 20° C. and is then poured slowly into a saturated aqueous solution of sodium bicarbonate; the mixture obtained is extracted 3 times with methylene chloride (400 cc in total). The organic phases are combined, dried over magnesium sulphate and filtered and the filtrate is concentrated to dryness under reduced pressure (2.7 kPa) at 30° C. The residue obtained is purified by "flash" chromatography [eluent: chloroform/methanol (96/4 by volume)]; fractions 5 and 6 are combined and concentrated to dryness under reduced pressure (2.7 kPa) at 30° C. This gives 5δ-(2-dimethylaminoethyl)thiomethylenepristinamycin I$_A$ (0.8 g) in the form of a yellow powder melting at about 150° C.

NMR spectrum: 0.68 (dd; 1H: 5β$_2$), 2.32 (s; 6H×0.85: —CH$_2$N(CH$_3$)$_2$ 1st isomer), 2.35 (s; 6H×0.15: —CH$_2$N(CH$_3$)$_2$ 2nd isomer), 2.45 (d; 1H×5β$_1$), 2.65 (mt; 2H: —SCH$_2$—), 3.05 (t; 2H: —CH$_2$N<), 3.43 (dd; 1H: 5ε$_2$), 5.15 (in unresolved peaks: 5ε$_1$), 7.60 (s broad; 1H: =CHS—), 7.83 (mt; 1H: 1′H$_6$ two isomers).

A 1% aqueous solution of 5δ-(2-dimethylaminoethyl)thiomethylenepristinamycin I$_A$ (product AX) in the form of the hydrochloride is obtained with:
  product AX: 0.1 g
  0.1N hydrochloric acid: 1 cc
  distilled water: q.s. 10 cc

EXAMPLE 29

By following a procedure analogous to that described in Example 28, but starting from 5δ-dimethylaminomethylenepristinamycin I$_A$ (3.68 g) and 2-diethylaminoethanethiol) (8.5 g), and after purification by "flash" chromatography [eluent: chloroform/methanol (96/4 by volume)] and concentration to dryness of fractions 13 to 20 under reduced pressure (2.7 kPa) at 30° C., 5δ-(2-diethylaminoethyl)thiomethylenepristinamycin I$_A$ (0.85 g) is obtained in the form of a beige powder melting at about 192° C.

NMR spectrum: 0.65 (dd; 1H: 5β$_2$), 1.05 (t; 6H: —N(CH$_2$CH$_3$)$_2$), 2.42 (d; 1H: 5β$_1$), 2.60 (q; 4H: —N(CH$_2$CH$_3$)$_2$), 3.42 (dd; 1H: 5ε$_2$), 5.10 (under unresolved peaks, 1H: 5ε$_1$), 7.58 (s broad; 1H: =CH—S—), 7.82 (dd; 1H×0.95: 1′H$_6$ 1st isomer), 7.98 (dd; 1H×0.05: 1′H$_6$ 2nd isomer).

A 1% aqueous solution of 5δ-(2-diethylaminoethyl)thiomethylenepristinamycin I$_A$ (product AY) in the form of the hydrochloride is obtained with:
  product AY: 0.04 g
  0.1N hydrochloric acid: 0.4 cc
  distilled water: q.s. 4 cc

EXAMPLE 30

By following a procedure analogous to that described in Example 28, but starting from 5δ-dimethylaminomethylenepristinamycin I$_A$ (3g) and 3-dimethylaminopropanethiol (0.4 g), and after purification by "flash" chromatography [eluent: chloroform/methanol (92.5/7.5 by volume)] and concentration to dryness of fractions 10 to 17 under reduced pressure (2.7 kPa) at 30° C., 5δ-(3-dimethylaminopropyl)thiomethylenepristinamycin I$_A$ (0.85 g) is obtained in the form of a beige powder melting at about 170° C.

NMR spectrum: 0.70 (dd; 1H: 5β$_2$), 1.90 (up; 2H: —S—CH$_2$CH$_2$CH$_2$N<), 2.20 (s; 6H: —N(CH$_3$)$_2$), 2.40 (d; 1H: 5β$_1$), 2.90 (up; 2H: —CH$_2$—N<), 3.45 (dd; 1H: 5ε$_2$), 7.65 (s broad; 1H: =CH—S—).

A 1% aqueous solution of 5δ-(3-dimethylaminopropyl)thiomethylenepristinamycin I$_A$ (product AZ) in the form of the hydrochloride is obtained with:
  product AZ: 0.03 g
  0.1N hydrochloric acid: 0.3 cc
  distilled water: q.s. 3 cc

EXAMPLE 31

By following a procedure analogous to that described in Example 28, but starting from 5δ-dimethylaminomethylenevirginiamycin S (1.8 g) and 3-dimethylaminopropanethiol (0.48 g), and after purification by "flash" chromatography [eluent: chloroform/methanol (95/5 by volume)] and concentration to dryness of fractions 5 to 14 under reduced pressure (2.7 kPa) at 30° C., 5δ-(3-dimethylaminopropyl)thiomethylenevirginiamycin S (0.7 g) is obtained in the form of a beige powder melting at about 140° C.

NMR spectrum: 0.50 (dd; 1H: 5β$_2$), 2 (up; 2H: —SCH$_2$—CH$_2$—CH$_2$N<), 2.35 (s; 6H: —S(CH$_2$)$_3$N(CH$_3$)$_2$), 2.60 (t; 2H: —SCH$_2$—CH$_2$CH$_2$—N<), 3 (t; 2H: —SCH$_2$CH$_2$CH$_2$N<), 3.35 (dd; 1H: 5ε$_2$), 4.90 (dd; 1H: 5ε$_1$), 5.20 (up; 1H: 5α), 7.60 (s broad; 1H: =CH—S—), 7.80 (dd; 1H: 1′H$_6$).

A 10% aqueous solution of 5δ-(3-dimethylaminopropyl)thiomethylenevirginiamycin S (product AAA) in the form of the hydrochloride is obtained with:
  product AAA: 0.1 g
  0.2N hydrochloric acid: 0.52 cc
  distilled water: q.s. 1 cc

EXAMPLE 32

By following a procedure analogous to that described in Example 28, but starting from 5δ-dimethylaminomethylenepristinamycin I$_A$ (4 g) and 3-dimethylamino-2-methylpropanethiol (0.7 g), and after purification by "flash" chromatography [eluent: chloroform/methanol (94/6 by volume)] and concentration to dryness under reduced pressure (2.7 kPa) at 30° C., 5δ-(3-dimethylamino-2-methylpropyl)thiomethylenepristinamycin I$_A$ (0.96 g) is obtained in the form of a beige powder melting at 234° C.

NMR spectrum: 0.65 (dd; 1H: 5β$_2$), 1.05

(d; 3H: —CHCH$_3$)

2.25 (s; 6H: —N(CH$_3$)$_2$), 2.40 (d; 1H: 5β$_1$), 3.15 and 2.90 (ABX system, 2H: —CH$_2$N<), 3.45 (d broad; 2H: 5ε), 7.75 (dd; 1H×0.80: 1'H$_6$ 1st isomer), 7.95 (dd; 1H×0.20: 1'H$_6$ 2nd isomer).

A 1% aqueous solution of 5δ-(3-dimethylamino-2-methylpropyl)thiomethylenepristinamycin I$_A$ (product AAB) in the form of the hydrochloride is obtained with:
  product AAB: 0.03 g
  0.1N hydrochloric acid: 0.3 cc
  distilled water: q.s. 3 cc The 3-dimethylamino-2-methylpropanethiol can be prepared in the following manner:

Sodium (0.026 g) is added to a solution of N,N-dimethyl-3-acetylthio-2-methylpropylamine (5.33 g) in anhydrous methanol (50 cc). The mixture obtained is heated under reflux for 7 hours and the methanol is then removed under reduced pressure (2.7 kPa) at 50° C. The residue is distilled under reduced pressure (2.7 kPa). This gives 3-dimethylamino-2-methylpropanethiol (0.9 g) in the form of a yellow oil distilling at 56° C. under 2.7 kPa.

The N,N-dimethyl-3-acetylthio-2-methylpropylamine can be prepared in the following manner:

Thiolacetic acid (15.7 cc) is added to a solution of N,N-dimethyl-1-chloro-2-methylpropylamine (29.5 g) in isopropanol (120 cc). The mixture obtained is heated under reflux for 48 hours and the isopropanol is then removed under reduced pressure (2.7 kPa) at 60° C. The residue obtained is treated with a saturated aqueous solution of sodium bicarbonate (100 cc) and the aqueous phase is extracted 3 times with ethyl ether (600 cc in total). The organic phases are combined, dried over magnesium sulphate and filtered and the filtrate is concentrated to dryness. The residue obtained is purified by "flash" chromatography [eluent: chloroform/methanol (90/10 by volume)]; fractions 6 to 10 are combined and concentrated to dryness under reduced pressure (2.7 kPa) at 30° C. This gives N,N-dimethyl-3-acetylthio-2-methylpropylamine (5.57 g) in the form of a red oil.

The N,N-dimethyl-1-chloro-2-methylpropylamine can be prepared according to the method described by J. P. BOURQUIN et al., Helv. Chim. Acta, 41, 1072 (1958).

EXAMPLE 33

By following a procedure analogous to that described in Example 28, but starting from 5δ-dimethylaminomethylenepristinamycin I$_A$ (4 g) and 2-dimethylamino-2-methylpropanethiol (1.14 g), and after purification by "flash" chromatography [eluent: chloroform/methanol (92/8 by volume)] and concentration to dryness of fractions 12 to 30 under reduced pressure (2.7 kPa) at 30° C., 5δ-(2-dimethylamino-2-methylpropyl)thiomethylenepristinamycin I$_A$ (1.4 g) is obtained in the form of a beige powder melting at about 200° C.

NMR spectrum: 0.55 (dd; 1H×0.20: 5β$_2$ 2nd isomer), 0.68 (dd; 1H×0.80: 5β$_2$ 1st isomer), 1.15 (s, 6H: —C(CH$_3$)$_2$—), 2.30 (s; 6H×0.80: —N(CH$_3$)$_2$ 1st isomer), 2.42 (s; 6H×0.20: —N(CH$_3$)$_2$ 2nd isomer), 2.40 (d; 1H: 5β$_1$), 2.80 (under unresolved peaks: —S—CH$_2$—), 3.42 (dd; 1H: 5ε$_2$), 7.55 (s broad: 1H: =CH—S), 7.80 (dd; 1H×0.80: 1'H$_6$ 1st isomer), 7.98 (dd; 1H×0.20: 1'H$_6$ 2nd isomer).

A 1% aqueous solution of 5δ-(2-dimethylamino-2-methylpropyl)thiomethylenepristinamycin I$_A$ (product AAC) in the form of the hydrochloride is obtained with:
  product AAC: 0.03 mg
  hydrochloric acid: 0.3 ml
  distilled water: q.s. 3 ml The 2-dimethylamino-2-methylpropanethiol can be prepared according to the method described by H. R. SNYDER, J. M. STEWART and J. B. ZIEGLER, J. Am. Chem. Soc., 69, 2672 (1947).

EXAMPLE 34

By following a procedure analogous to that described in Example 28, but starting from 5δ-dimethylaminomethylenepristinamycin I$_A$ (4 g) and 2-(pyrrolidin-1-yl)ethanethiol (1.1 g), and after purification by "flash" chromatography [eluent: chloroform/methanol (96/4 by volume)] and concentration to dryness of fractions 9 to 15 under reduced pressure (2.7 kPa) at 30° C., 5δ-[2-(pyrrolidin-1-yl)ethyl]thiomethylenepristinamycin I$_A$ (1.3 g) is obtained in the form of a beige powder melting at about 180° C.

NMR spectrum: 0.65 (dd; 1H: 5δ$_2$), 1.85

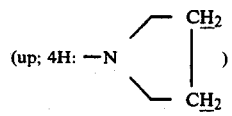

2.45 (d; 1H: 5β$_1$), 2.75 and 2.90

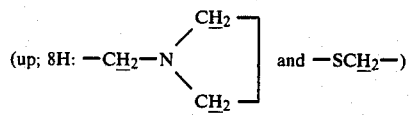

3.45 (dd; 1H: 5ε$_2$), 7.60 (s broad; 1H: =CH—S—), 7.85 (dd; 1H: 1'H$_6$).

A 1% aqueous solution of 5δ-[2-(pyrrolidin-1-yl)ethyl]thiomethylenepristinamycin I$_A$ (product AAD) in the form of the hydrochloride is obtained with:
  product AAD: 0.03 g
  0.1N hydrochloric acid: 0.3 ml
  distilled water: q.s. 3 ml The 2-(pyrrolidin-1-yl)ethanethiol can be prepared according to the method described by J. W. HAEFFELE and R. W. BROGE, Proc. Sci. Toilet Goods Assoc. 32, 52 (1959) [Chem. Abstr. 54, 17234e (1960)].

EXAMPLE 35

By following a procedure analogous to that described in Example 28, but starting from 5δ-dimethylaminomethylenepristinamycin I$_A$ (4 g) and 2-(1-methylpyrrolidin-2-yl)ethanethiol (1.74 g), and after purification by "flash" chromatography [eluent: chloroform/methanol (92/8 by volume)] and concentration to dryness of fractions 12 to 22 under reduced pressure (2.7 kPa) at 30° C., 5δ-[2-(1-methylpyrrolidin-2-yl)ethyl]thiomethylenepristinamycin I$_A$ (1.33 g) is obtained in the form of a biege powder melting at about 215° C.

NMR spectrum: 0.65 (dd; 1H: 5β$_2$), 1.4–2.3

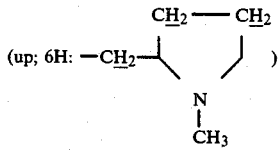

2.40 (d; 1H: 5β$_1$), 2.48 (s; 3H: >N—CH$_3$ pyrrolidine), 3.40 (dd; 1H: 5ε$_2$), 7.50 (s broad; 1H: =CH—), 7.80 (dd;

1H×0.85: 1'H₆ 1st isomer), 8.00 (dd; 1H×0.15: 1'H₆ 2nd isomer).

A 0.6% aqueous solution of 5δ-[2-(1-methylpyrrolidin-2-yl)ethyl]thiomethylenepristinamycin I$_A$ (product AAE) in the form of the hydrochloride is obtained with:
- product AAE: 0.03 g
- 0.1N hydrochloric acid 0.3 cc
- distilled water: q.s. 5 cc The 2-(1-methylpyrrolidin-2-yl)ethanethiol can be prepared by a procedure analogous to that described in Example 32 for preparing 3-dimethylamino-2-methylpropanethiol, but starting from 2-(2-acetylthioethyl)-1-methylpyrrolidine (15.7 g) and sodium (0.07 g). This gives a product (12.2 g) in the form of a red oil.

The 2-(2-acetylthioethyl)-1-methylpyrrolidine can be prepared by a procedure analogous to that described in Example 32 for preparing N,N-dimethyl-3-acetylthio-2-methylpropylamine, but starting from 2-(2-chloroethyl)-1-methylpyrrolidine (12.7 g) and thiolacetic acid (6.8 cc). This gives a product (15.7 g) in the form of a red oil.

EXAMPLE 36

By following a procedure analogous to that described in Example 28, but starting from 5δ-dimethylaminomethylenepristinamycin I$_A$ (3.0 g) and 4-mercapto-1-methylpiperidine (0.48 g), and after purification by "flash" chromatography [eluent: chloroform/methanol (90/10 by volume)] and concentration to dryness of fractions 15 to 19 under reduced pressure (2.7 kPa) at 30° C., 5δ-(1-methylpiperidin-4-yl)thiomethylenepristinamycin I$_A$ (1.2 g) is obtained in the form of a yellow powder melting at about 170° C.

NMR spectrum: 0.68 (dd; 1H: 5β₂), 2.0–2.2

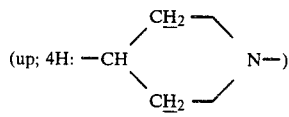

2.30 (s; 3H: >N—CH₃), 2.45 (d; 1H: 5β₁), 2.85

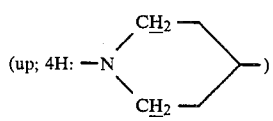

3.05

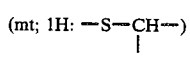

3.40 (dd; 1H: 5ε₂), 5.15 (d; 1H: 5ε₁), 7.67 (s broad; 1H: =CH—S—), 7.85 (dd; 1H×0.85: 1'H₆ 1st isomer), 8.0 (dd; 1H×0.15: 1'H₆ 2nd isomer).

A 1% aqueous solution of 5δ-(1-methylpiperidin-4-yl)thiomethylenepristinamycin I$_A$ (product AAF) in the form of the hydrochloride is obtained with:
- product AAF: 0.05 g
- 0.1N hydrochloric acid: 0.5 cc
- distilled water: q.s. 5 cc The 4-mercapto-1-methylpiperidine can be prepared according to the method described by H. BARRER and R. E. LYLE, J. Org. Chem. 27, 641 (1962).

EXAMPLE 37

By following a procedure analogous to that described in Example 28, but starting from 5δ-dimethylaminomethylenepristinamycin I$_A$ (4 g) and 1-ethyl-3-mercaptopiperidine (0.8 g), and after purification by "flash" chromatography [eluent: chloroform/methanol (92/8 by volume)] and concentration to dryness of fractions 6 to 9 under reduced pressure (2.7 kPa) at 30° C., 5δ-(1-ethylpiperidin-3-yl)thiomethylenepristinamycin I$_A$ (1.1 g) is obtained, which melts about 175° C.

NMR spectrum: 0.70 (s broad, 1H: 5β₂), 1.20 (t; 3H: —CH₂CH₃), 2.45 (d broad; 1H: 5β₁), 2.90

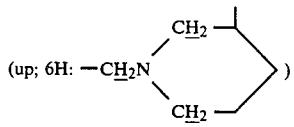

7.50 (s broad; 1H: =CH—S—), 7.80 (dd; 1H×0.80: 1'H₆ 1st isomer), 7.95 (dd; 1H×0.20: 1'H₆ 2nd isomer).

A 1% aqueous solution of 5δ-(1-ethylpiperidin-3-yl)thiomethylenepristinamycin I$_A$ (product AAG) in the form of the hydrochloride is obtained with:
- product AAG: 0.03 g
- 0.1N hydrochloric acid: 0.3 cc
- distilled water: q.s. 3 cc The 1-ethyl-3-mercaptopiperidine can be prepared according to the method described by J. H. BIEL et al., J. Am. Chem. Soc. 77, 2250 (1955).

EXAMPLE 38

By following a procedure analogous to that described in Example 28, but starting from 5δ-dimethylaminomethylenepristinamycin I$_A$ (3.0 g) and N-(2-mercaptoethyl)-N,N',N'-trimethylethylenediamine (0.55 g), and after purification by "flash" chromatography [eluent: chloroform/methanol (90/10 by volume)] and concentration to dryness of fractions 17 to 24 under reduced pressure (2.7 kPa) at 30° C., 5δ-[2-(2-dimethylaminoethyl)methylaminoethyl]thiomethylenepristinamycin I$_A$ (1.0 g) is obtained in the form of a yellow powder melting to about 160° C.

NMR spectrum: 0.68 (dd; 1H: 5β₂), 2.30

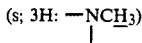

2.40 (d; 1H: 5β₁), 2.4–3.1 (up; 8H: —S(CH₂)₂N—(CH₂)₂N<), 3.40 (dd; 1H: 5ε₂), 5.10 (under unresolved peaks; 1H: 5ε₁), 7.58 (s broad; 1H: =CH—S—), 7.80 (dd; 1H: 1'H₆).

A 1% aqueous solution of 5δ-[2-(2-dimethylaminoethyl)methylaminoethyl]thiomethylenepristinamycin I$_A$ (product AAH) is obtained with:
- product AAH: 0.03 g
- distilled water: q.s. 3 cc The N-(2-mercaptoethyl)-N,N',N'-trimethylethylenediamine can be prepared in the following manner: ethyl 2-mercaptoethyl carbonate (5.0 g) is added to a solution of N,N',N'-trimethylethylenediamine (10.2 g) in toluene (40 cc), heated under reflux. After 5 hours under reflux, the toluene is removed under reduced pressure (2.7 kPa) at 50° C. and the residue is distilled at this pressure. This gives N-(2-mercaptoethyl)-N,N',N'- trimethylethylenediamine in the form of a yellow liquid distilling at 105° C. under 2.7 kPa.

The ethyl 2-mercaptoethyl carbonate can be prepared according to the method described by D. D. REYNOLDS, D. L. FIELDS and D. L. JOHNSON, J. Org. Chem. 26, 5125 (1961).

EXAMPLE 39

By following a procedure analogous to that described in Example 28, but starting from 5δ-dimethylaminomethylenepristinamycin I$_A$ (4 g) and 1,3-bis(dimethylamino)propane-2-thiol (2 g), and after purification by "flash" chromatography [eluent: chloroform/methanol (92/8 by volume)] and concentration to dryness of fractions 32 to 56 under reduced pressure (2.7 kPa) at 30° C., 5δ-[1,3-bis(dimethylamino)prop-2-yl]thiomethylenepristinamycin I$_A$ (1.6 g) is obtained in the form of a beige powder melting at about 190° C.

NMR spectrum: 0.55 (dd; 1H×0.80: 5$\beta_2$ 2nd isomer), 0.67 (dd; 1H×0.20: 5$\beta_2$ 1st isomer), 2.30 (up; 6H: —N(C$\underline{H}_3$)$_2$), 2.8–3.2 (up; 4H: —SCH(C$\underline{H}_2$N<)$_2$), 7.62 (up; 1H: =C$\underline{H}$—S—), 7.80 (dd; 1H×0.80: 1'H$_6$ 1st isomer), 7.98 (dd; 1H×0.20: 1'H$_6$ 2nd isomer).

A 1% aqueous solution of 5δ-[1,3-bis(dimethylamino)prop-2-yl]thiomethylenepristinamycin I$_A$ (product AAI) in the form of the hydrochloride is obtained with:

product AAI: 0.03 g
0.1N hydrochloric acid: 0.3 cc
distilled water: q.s. 3 cc

The 1,3-bis(dimethylamino)propane-2-thiol can be prepared according to the method described by J. M. STEWART, J. Org. Chem., 29, 1655 (1964).

EXAMPLE 40

By following a procedure analogous to that described in Example 28, but starting from 5δ-dimethylaminomethylenepristinamycin I$_A$ (3.0 g) and 1-(2-mercaptoethyl)-4-methylpiperazine (0.58 g), and after purification by "flash" chromatography [eluent: chloroform/methanol (87.5/12.5 by volume)] and concentration to dryness of fractions 16 to 30 under reduced pressure (2.7 kPa) at 30° C., 5δ-[2-(4-methylpiperazin-1-yl)ethyl]thiomethylenepristinamycin I$_A$ (1.6 g) is obtained in the form of a beige powder melting about 170° C.

NMR spectrum: 0.56 (dd; 1H×0.20: 5$\beta_2$ 1st isomer), 0.68 (dd; 1H×0.80: 5$\beta_2$ 2nd isomer), 2.40 (s; 3H: >NCH$_3$), 2.5–3 (up; 12H: —S(CH$_2$)$_2$N<+all the —C$\underline{H}_2$— of piperazine), 3.42 (dd; 1H: 5$\epsilon_2$), 5.12 (d broad; 5$\epsilon_1$), 7.60 (s broad; 1H: =CHS—), 7.80 (dd; 1H: 1'H$_6$, mixture of the 2 isomers).

A 1% aqueous solution of 5δ-[2-(4-methylpiperazin-1-yl)ethyl]thiomethylenepristinamycin I$_A$ (product AAJ) in the form of the hydrochloride is obtained with:

product AAJ: 0.05 g
0.1N hydrochloric acid: 0.5 cc
distilled water: q.s. 5 cc

The 1-(2-mercaptoethyl)-4-methylpiperazine can be prepared according to the method described by D. D. REYNOLDS et al., J. Org. Chem. 26, 5125 (1961).

EXAMPLE 41

By following a procedure analogous to that described in Example 28, but starting from 5δ-dimethylaminomethylenepristinamycin I$_A$ (4.0 g) and 1-(3-mercaptopropyl)-4-methylpiperazine (1.5 g), and after purification by "flash" chromatography [eluent: chloroform/methanol (95/5 by volume)] and concentration to dryness of fractions 24 to 41 under reduced pressure (2.7 kPa) at 30° C., 5δ-[3-(4-methylpiperazin-1-yl)propyl]thiomethylenepristinamycin I$_A$ (2.06 g) is obtained in the form of a biege powder melting at about 190° C.

NMR spectrum: 0.68 (dd; 1H: 5$\beta_2$), 1.90 (mt; 2H: —CH$_2$—C$\underline{H}_2$CH$_2$N<), 2.40 (s; 3H: >NCH$_3$), 2.3 to 2.8

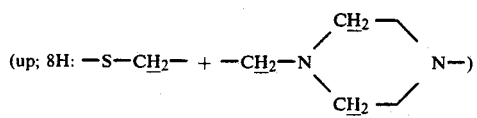

3.45 (up; 1H: 5$\epsilon_2$), 7.64 (s broad; 1H×0.80: =CH—S— 1st isomer), 7.70 (s broad; 1H×0.20: =CH—S— 2nd isomer), 7.80 (dd; 1H×0.80: 1'H$_6$ 1st isomer), 7.98 (dd; 1H×0.20: 1'H$_6$ 2nd isomer).

A 10% aqueous solution of 5δ-[3-(4-methylpiperazin-1-yl)propyl]thiomethylenepristinamycin I$_A$ (product AAK) in the form of the hydrochloride is obtained with:

products AAK: 0.05 g
0.1N hydrochloric acid: q.s. 0.5 ml

The 1-(3-mercaptopropyl)-4-methylpiperazine can be prepared in a manner analogous to that described in Example 32 for preparing 3-dimethylamino-2-methylpropanethiol, but starting from 1-(3-acetylthiopropyl)-4-methylpiperazine (109 g) and sodium (0.46 g). This gives 1-(3-mercaptopropyl)-4-methylpiperazine (64.8 g) in the form of a yellow oil distilling at 133° C. under 0.13 kPa.

The 1-(3-acetylthiopropyl)-4-methylpiperazine can be prepared in a manner analogous to that described in Example 32 for preparing N,N-dimethyl-3-acetylthio-2-methylpropylamine, but starting from 1-(3-chloropropyl)-4-methylpiperazine (138 g) and thiolacetic acid (68.5 g). This gives 1-(3-acetylthiopropyl)-4-methylpiperazine (109 g) in the form of a yellow oil distilling at about 160° C. under 0.13 kPa.

EXAMPLE 42

By following a procedure analogous to that described in Example 28, but starting from 5δ-dimethylaminomethylenepristinamycin I$_A$ (4.0 g) and 3-mercapto-2-methylpropylammonium iodide (1.3 g), and after purification by "flash" chromatography [eluent: chloroform/methanol (80/20 by volume)] and concentration to dryness of fractions 12 to 22 under reduced pressure (2.7 kPa) at 30° C., 5δ-(2-methyl-3-trimethylammoniopropyl)thiomethylenepristinamycin I$_A$ iodide (1.05 g) is obtained in the form of an ochre powder melting at about 150° C.

NMR spectrum: 1.05–1.35

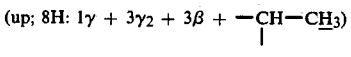

2.40

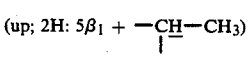

2.90 (mt; 3H: 4$\beta_2$+—S—C$\underline{H}_2$—), 3.20

(mt; 7H: 4NCH$_3$ + 4$\beta_1$ + 3$\delta_1$ + —C$\underline{H}_2$N(CH$_3$)$_3$)
$\overset{\oplus}{}$ 3.40 (mt; 9H: —$\overset{\oplus}{\text{N}}$ (C$\underline{H}_3$)$_3$).

A 1% aqueous solution of 5δ-(2-methyl-3-trimethylammoniopropyl)thio methylenepristinamycin I$_A$ iodide (product AAL) in the form of the hydrochloride is obtained with:
 product AAL: 0.02 g
 0.1N hydrochloric acid: 0.2 cc
 distilled water: q.s. 2 cc The 3-mercapto-2-methylpropylammonium iodide can be prepared in the following manner: sodium methylate (0.024 g) is added to a solution of 3-acetylthio-2-methylpropylammonium iodide (3.6 g) in methanol (18 cc) at a temperature of the order of 20° C. The mixture obtained is heated under reflux for 1 hour and then left at ambient temperature for 16 hours. The methanol is removed under reduced pressure (2.7 kPa) at 50° C. The residue is stirred for 1 hour with isopropanol (35 cc), the white suspension is filtered and the material on the filter is then dried. This gives 3-mercapto-2-methylpropylammonium iodide (3.1 g) in the form of a beige powder melting at 120° C.

The 3-acetylthio-2-methylpropylammonium iodide can be prepared in the following manner: methyl iodide (1.4 cc) is added to a solution of N,N-dimethyl-3-acetylthio-2-methylpropylamine (3.5 g) in acetonitrile (35 cc); after stirring for 18 hours at a temperature of the order of 20° C., the precipitate is filtered off and then dried. This gives 3-acetylthio-2-methylpropylammonium iodide (3.8 g) in the form of a white powder melting at 181° C.

EXAMPLE 43

By following a procedure analogous to that described in Example 28, but starting from 5δ-dimethylaminomethylenepristinamycin I$_A$ (1.84 g) and the sodium salt of 2-mercaptoethanesulphonic acid (3.28 g), and after purification by "flash" chromatography [eluent: methylene chloride/methanol (90/10 by volume)] and concentration to dryness of fractions 6 to 14 under reduced pressure (2.7 kPa) at 30° C., 5δ-(2-hydroxysulphonylethyl)thiomethylenepristinamycin I$_A$ (0.8 g) is obtained in the form of a yellow powder melting at a temperature above 280° C.

The infra-red spectrum contains the bands characteristic of pristinamycins: 1745, 1680, 1650, 1525, 815, 740 and 705 cm$^{-1}$, plus the bands characteristic of the group —SO$_3$H [1200 cm$^{-1}$ (broad) and 1050 cm$^{-1}$].

A 5% aqueous solution of 5δ-(2-hydroxysulphonylethyl)thiomethylenepristinamycin I$_A$ (product AAM) is obtained with:
 product AAM: 0.1 g
 distilled water: q.s. 2 cc

EXAMPLE 44

A solution of 5δ-(4-methylphenyl)sulphonyloxymethylenepristinamycin I$_A$ (5.2 g) in methylene chloride (50 cc) is added to a solution of 1-(2-mercaptopropyl)-4-methylpiperazine (0.87 g) in ethanol (50 cc), to which sodium ethylate (0.34 g) has been added. The reaction mixture is stirred for 16 hours at a temperature of the order of 20° C. and then diluted with methylene chloride (500 cc) and distilled water (100 cc). After stirring, the aqueous phase is extracted twice with methylene chloride (50 cc in total). The organic phases are combined, dried over magnesium sulphate and filtered and the filtrate is then concentrated to dryness under reduced pressure (2.7 kPa) at 30° C. The residue is purified by "flash" chromatography [eluent: chloroform/methanol (97.5/2.5 by volume)]. Fractions 33 to 80 are combined and concentrated to dryness under reduced pressure (2.7 kPa) at 30° C. This gives 5δ-[3-(4-methylpiperazin-1-yl)prop-2-yl]thiomethylenepristinamycin I$_A$ (1.25 g) in the form of a beige powder melting at about 195° C.

NMR spectrum: 0.70 (dd; 1H: 5$\beta_2$), 1.25

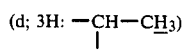

2.30 (s; 3H: >N—C$\underline{H}_3$), 2.50

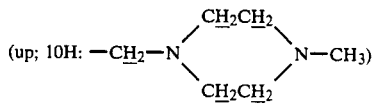

3.40 (dd; 1H: 5ε$_2$), 7.85 (dd broad; 1H: 1'H$_6$).

A 10% aqueous solution of 5δ-[3-(4-methylpiperazin-1-yl)prop-2-yl]thiomethylenepristinamycin I$_A$ (product AAN) in the form of the hydrochloride is obtained with:
 product AAN 0.03 g
 0.1N hydrochloric acid 0.3 cc The 1-(2-mercaptopropyl)-4-methylpiperazine is prepared by heating a mixture of propylene sulphide (19 cc) and N-methylpiperazine (29 cc) at 100° C. for 16 hours. This gives a colourless oil (32 g) distilling at 105° C. under 1.3 kPa.

The 5δ-(4-methylphenyl)sulphonyloxymethylenepristinamycin I$_A$ can be obtained in the following manner:

Triethylamine (0.42 cc) and then p-toluenesulphonyl chloride (0.57 g) are added, at a temperature of the order of −30° C., to a solution of 5δ-hydroxymethylenepristinamycin I$_A$ (2.7 g) in methylene chloride (30 cc). The reaction mixture is subsequently stirred for 2 hours at a temperature of the order of 20° C. and then concentrated to dryness under reduced pressure (2.7 kPa) at 30° C.; the residue obtained is purified by "flash" chromatography [eluent: methylene chloride/methanol (96/4 by volume)]. After concentration to dryness of fractions 4 to 6 under reduced pressure (2.7 kPa) at 30° C., 5δ-(4-methylphenyl)sulphonyloxymethylenepristinamycin I$_A$ (2.2 g) is obtained in the form of a white powder melting at about 265° C.

NMR spectrum: 0.50 (dd; 1H: 5$\beta_2$), 2.35

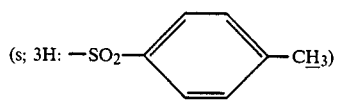

3.30 (dd; 1H: 5ε$_2$), 5.25 (d; 1H: 5α), 5.30 (dd; 1H: 5ε$_1$), 7.35 to 7.90

(AB system + up; 8H: 4δ + 4ε + —SO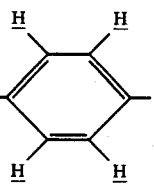

7.85 (dd; 1H: 1'H<sub>6</sub>).

The 5δ-hydroxymethylenepristinamycin I<sub>A</sub> can be prepared in the following manner:

5δ-Dimethylaminomethylenepristinamycin I<sub>A</sub> (10.6 g) is added, with stirring, to a 0.1N aqueous solution of hydrochloric acid (420 cc). The solution obtained is then stirred for 3 hours at a temperature of the order of 20° C. A saturated aqueous solution of sodium bicarbonate (30 cc) is then added dropwise so as to give a pH of the order of 4. The product which precipitates is filtered off and then washed 3 times with distilled water (30 cc in total). After drying under reduced pressure (2.7 kPa) at a temperature of the order of 20° C., 5δ-hydroxymethylenepristinamycin I<sub>A</sub> (9.5 g) is obtained in the form of a beige powder. This product is of sufficient quality to be used as such in the subsequent stages. However, it can be purified in the following manner:

Crude 5δ-hydroxymethylenepristinamycin I<sub>A</sub> (9.5 g) is dissolved in ethyl acetate (50 cc); the solution obtained is poured onto silica gel (100 g) contained in a column of diameter 2.8 cm. Elution is carried out initially with ethyl acetate (400 cc) and the corresponding eluate is discarded; elution is continued with ethyl acetate (1600 cc) and the corresponding eluate is concentrated to dryness under reduced pressure (2.7 kPa) at 30° C. This gives 5δ-hydroxymethylenepristinamycin I<sub>A</sub> (6.3 g) in the form of white crystals melting at 220° C.

NMR spectrum: 0.69 (dd; 1H: 5β<sub>2</sub>), 2.43 (d; 1H: 5β<sub>1</sub>), 3.40 (d; 1H: 5ε<sub>2</sub>), 4.0 to 4.2 (up; 3H: 4α+5ε<sub>1</sub>+5α), 8.15 (s; 1H: =CH—OH), 11.63 (s broad; 1H: =CH—OH).

EXAMPLE 45

By following a procedure analogous to that described in Example 44, but starting from 5δ-(4-methylphenyl)-sulphonyloxymethylenepristinamycin I<sub>A</sub> (5.2 g), 1-dimethylaminopropane-2-thiol (0.6 g) and sodium ethylate (0.34 g), and after purification by "flash" chromatography [eluent: chloroform/methanol (95/5 by volume)] and concentration to dryness of fractions 16 to 38 under reduced pressure (2.7 kPa) at 30° C., 5δ-(3-dimethylaminoprop-2-yl)thiomethylenepristinamycin I<sub>A</sub> (1 g) is obtained in the form of a yellow powder melting at 172° C.

NMR spectrum: 0.65 (dd; 1H: 5β<sub>2</sub>), 1.10

(d; 3H: —CH—CH<sub>3</sub>)

2.30 (s; 6H: —N(CH<sub>3</sub>)<sub>2</sub>), 7.60 (s broad; 1H: =CH—S—), 7.85 (dd; 1H: 1'H<sub>6</sub>).

A 5% aqueous solution of 5δ-(3-dimethylaminoprop-2-yl)thiomethylenepristinamycin I<sub>A</sub> (product AAO) in the form of the hydrochloride is obtained with:

product AAO: 0.03 g
0.1N hydrochloric acid: 0.3 cc
distilled water: q.s. 0.6 cc

The 1-dimethylaminopropane-2-thiol can be prepared according to the method described by S. D. TURK et al., J. Org. Chem. 29, 974 (1964).

EXAMPLE 46

By following a procedure analogous to that described in Example 44, but starting from 5δ-(4-methylphenyl)-sulphonyloxymethylenepristinamycin I<sub>A</sub> (6.3 g), 5-diethylaminopentane-2-thiol (1.05 g) and sodium ethylate (0.408 g), and after purification by "flash" chromatography [eluent: chloroform/methanol (97.5/2.5 by volume)] and concentration to dryness of fractions 47 to 65 under reduced pressure (2.7 kPa) at 30° C., 5δ-(5-diethylaminopent-2-yl)thiomethylenepristinamycin I<sub>A</sub> (1.32 g) is obtained in the form of a beige powder melting at about 185° C.

NMR spectrum: 0.65 (dd; 1H: 5β<sub>2</sub>), 1.20 (t; 6H: —N(CH<sub>2</sub>CH<sub>3</sub>)<sub>2</sub>), 1.40

(d; 3H: —CH—CH<sub>3</sub>)

1.70 (s broad; 4H: —CH(CH<sub>2</sub>)<sub>2</sub>—CH<sub>2</sub>N<), 2.65 (q; 4H: —N(CH<sub>2</sub>—CH<sub>3</sub>)<sub>2</sub>), 3.50 (dd; 1H: 5ε<sub>2</sub>), 7.65 (s broad; 1H: =CH—S—), 7.85 (dd; 1H: 1'H<sub>6</sub>).

A 10% aqueous solution of 5δ-(5-diethylaminopent-2-yl)thiomethylenepristinamycin I<sub>A</sub> (product AAP) in the form of the hydrochloride is obtained with:

product AAP: 0.05 g
0.1N hydrochloric acid: 0.5 cc

The 5-diethylaminopentane-2-thiol can be prepared in a manner analogous to that described in Example 32 for preparing 3-dimethylamino-2-methylpropanethiol, but starting from N,N-diethyl-4-acetylthiopentan-1-amine (4.0 g) and sodium (0.046 g). After purification by "flash" chromatography [eluent: ethyl acetate/methanol (70/30 by volume)] and concentration to dryness of fractions 16 to 24, 5-diethylaminopentane-2-thiol (2.0 g) is obtained in the form of a yellow oil.

The N,N-diethyl-4-acetylthiopentan-1-amine can be prepared in a manner analogous to that described in Example 32 for preparing N,N-dimethyl-3-acetylthio-2-methylpropylamine, but starting from N,N-diethyl-4-chloropentan-1-amine (32 g) and thiolacetic acid (15.2 g). This gives a product (4.31 g) in the form of a yellow oil.

The N,N-diethyl-4-chloropentan-1-amine can be prepared according to the method described by M. S. KHARASH and C. F. FUCHS, U.S. Pat. No. 2,432,905.

EXAMPLE 47

A solution of 5δ-[(4-methylphenyl)sulphonyloxymethylene]pristinamycin I<sub>A</sub> (7.6 g) in tetrahydrofuran (60 cc) is cooled to a temperature of the order of −10° C. A solution of 2-dimethylaminoethanol (0.65 g) in tetrahydrofuran (60 cc), to which a 50% dispersion of sodium hydride in mineral oil (0.35 g) has been added, is added slowly to the first solution, the said temperature being maintained. When the addition has ended, the temperature is allowed to rise slowly to about 20° C. The reaction mixture is stirred for 24 hours at this temperature and then diluted with methylene chloride (500 cc) and washed with a saturated solution of ammonium chloride (2×50 cc). The organic phase is dried over magnesium sulphate and filtered and the filtrate is then concentrated to dryness under reduced pressure (2.7 kPa) at 40° C. The residue obtained is purified by "flash" chromatography [eluent: chloroform/methanol (95/5 by volume)]. Fractions 12 to 17 are combined and concentrated to dryness under reduced pressure (2.7 kPa) at 25° C. This gives 5δ-(2-dimethylaminoethoxymethylene)pristinamycin $I_A$ (1.5 g) in the form of a beige powder melting at about 160° C.

NMR spectrum: 0.65 (dd: 1H: $5\beta_2$), 2.3 (s; 6H: —N(C$\underline{H}_3$)$_2$), 2.65 (up; 2H: —C$\underline{H}_2$N<), 3.42 (dd; 1H: $5\epsilon_2$), 4.15 (t; 2H: —OC$\underline{H}_2$—), 5.15 (d; 1H: $5\epsilon_1$), 7.45 (under the aromatic protons; 1H: >C=C$\underline{H}$O—), 7.80 (dd; 1H: $1'H_6$).

A 1% aqueous solution of 5δ-(2-dimethylaminoethoxymethylene)pristinamycin $I_A$ (product AAQ) in the form of the hydrochloride is obtained with:

product AAQ: 0.03 g
0.1N hydrochloric acid: 0.3 cc
distilled water: q.s. 3 cc

EXAMPLE 48

4-Amino-1-methylpiperidine (0.12 g) is added, at a temperature of the order of 20° C., to a solution of 5δ-(4-methylphenyl)sulphonyloxymethylenepristinamycin $I_A$ (0.5 g) in ethanol (25 cc). After stirring for 16 hours at this temperature, the reaction mixture is diluted with methylene chloride (100 cc) and washed twice with distilled water (100 cc in total). The organic phase is dried over sodium sulphate and then concentrated under reduced pressure (2.7 kPa) at 30° C. The residue is stirred with ethyl ether (15 cc). After filtration, 5δ-(1-methylpiperidin-4-yl)aminomethylenepristinamycin $I_A$ (0.42 g) is obtained in the form of a white powder, the characteristics of which are identical to those described in Example 24.

EXAMPLE 49

By following a procedure analogous to those described in Examples 11 and 23, the following synergistine derivatives of the general formula (I) are prepared from a product of the general formula (IV) or of the general formula (IX):

| Starting material [Y = N(CH$_3$)$_2$] (—NR$_1$R$_2$ or —Z) | Reaction conditions | Product defined above in Example No. |
|---|---|---|
| —NR$_1$R$_2$ = —NH$_2$ | CH$_3$COOH, 20° C. 20 hours | 24 |
| —NR$_1$R$_2$ = —NHC$_{10}$H$_{21}$ | CH$_3$COOH, CF$_3$COOH, 20° C., 20 hours | 30 |
| —NR$_1$R$_2$ = —N⟨ (pyrrolidine) | CH$_3$COOH, 20° C. 20 hours | 24 |
| —NR$_1$R$_2$ = —NH—C$_6$H$_5$ | CH$_3$COOH, CF$_3$COOH, 20° C., 48 hours | 24 |
| —NR$_1$R$_2$ = —NH(CH$_2$)$_3$NH(CH$_2$)$_2$OH | CH$_3$COOH, CF$_3$COOH, 20° C., 20 hours | 30 |
| —NR$_1$R$_2$ = —NH(CH$_2$)$_3$N[(CH$_2$)$_2$OH]$_2$ | CH$_3$COOH, CF$_3$COOH, 20° C., 48 hours | 30 |
| —NR$_1$R$_2$ = —NH(CH$_2$)$_2$SH | CH$_3$COOH, 20° C., 20 hours | 30 |
| —NR$_1$R$_2$ = —NH(CH$_2$)$_2$NHC$_6$H$_5$ | CH$_3$COOH, 20° C., 10 days | 24 |
| —NR$_1$R$_2$ = | CH$_3$COOH, CF$_3$COOH, | 30 |

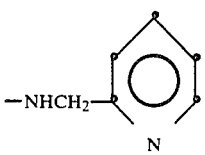

| Starting material [Y = N(CH$_3$)$_2$] (—NR$_1$R$_2$ or —Z) | Reaction conditions | Product defined above in Example No. |
|---|---|---|
| —NHCH$_2$-(pyridyl) | 20° C., 20 hours | |
| Z = —OCOCH$_3$ | CH$_3$COOH, 20° C., 6 hours | 24 |
| Z = —OPO(OC$_2$H$_5$)$_2$ | CH$_3$COOH, 20° C., 20 hours | 24 |

The products of the general formula (IV) used can be prepared as described below or by analogy with this method.

A 4N ethanolic solution of gaseous ammonia (10 cc) is added slowly to a solution of 5δ-dimethylaminomethylenepristinamycin $I_A$ (1.84 g) in acetic acid (20 cc). The solution obtained is stirred for 20 hours at a temperature of the order of 20° C. and then poured slowly into a saturated aqueous solution of sodium bicarbonate (200 cc). The suspension obtained is extracted 3 times with methylene chloride (300 cc in total); the organic phases are combined, dried over magnesium sulphate and filtered and the filtrate is concentrated to dryness under reduced pressure (2.7 kPa) at 30° C. The residue obtained is purified by "flash" chromatography [eluent: chloroform/methanol (92/8 by volume)]. By concentration to dryness of fractions 11 to 13 under reduced pressure (2.7 kPa) at 30° C., 5δ-aminomethylenepristinamycin $I_A$ (1.3 g) is obtained in the form of a beige powder melting at about 190° C.

NMR spectrum: 0.7 to 1.10 (mt, 4H: $2\gamma + 5\beta_2$), 7.15 to 7.53 (mt, 9H (including 1 exchangeable): $6\gamma + 6\delta + 6\epsilon + 1H$ of the NH$_2$+=C$\underline{H}$—NH$_2$+$1'H_4$+$1'H_5$), 9.12 (s broad, 1H (exchangeable): 1H of the NH$_2$).

The products of the general formula (IX) used can be prepared in the following manner:

5δ-acetoxymethylenepristinamycin $I_A$:

Acetyl chloride (0.14 cc) is added, at a temperature of the order of —20° C., to a solution of 5δ-hydroxymethylenepristinamycin $I_A$ (1.8 g) in methylene chloride (20 cc) containing triethylamine (0.2 g), and the temperature is then allowed to rise to about 20° C.

The reaction mixture is subsequently stirred for 20 hours at this temperature and then concentrated to dryness under reduced pressure (2.7 kPa) at 30° C.; the residue obtained is purified by "flash" chromatography [eluent: ethyl acetate]. After concentration to dryness of fractions 4 to 7 under reduced pressure (2.7 kPa) at 30° C., 5δ-acetoxymethylenepristinamycin $I_A$ (0.7 g) is obtained in the form of a yellow powder melting at about 160° C.

NMR spectrum: 0.60 (dd, 1H: $5\beta_2$), 2.25 (s, 3H: —CO—C$\underline{H}_3$), 2.45 (d, 1H: $5\beta_1$), 3.45 (dd, 1H: $5\epsilon_2$), 5.25 (dd, 1H: $5\alpha$), 5.45 (d, 1H: $5\epsilon_1$), 7.10 to 7.45 (up, 8H: $6\gamma + 6\delta + 6\epsilon + 1'H_4 + 1'H_5 + =C\underline{H}—O—$), 7.85 (dd, 1H: $1'H_6$).

5δ-diethoxyphosphoryloxymethylenepristinamycin $I_A$:

By following a procedure analogous to that described above, but starting from 5δ-hydroxymethylenepristinamycin I$_A$ (1.8 g) and diethyl chlorophosphate (0.34 g), and after purification by "flash" chromatography [eluent: ethyl acetate/methanol (90/10 by volume)] and concentration to dryness of fractions 6 to 14 under reduced pressure (2.7 kPa) at 30° C., 5δ-diethoxyphosphoryloxymethylenepristinamycin I$_A$ (0.8 g) is obtained in the form of a yellow powder melting at about 150° C.

NMR spectrum: 0.55 (dd, 1H: 5β$_2$), 1.30 (td, 6H: —PO(O—CH$_2$—CH$_3$)$_2$), 2.40 (d, 1H: 5β$_1$), 3.40 (dd, 1H: 5ε$_2$), 4.25 (ddd, 4H: —PO(O—CH$_2$—CH$_3$)$_2$), 5.25 (d, 1H: 5α), 5.40 (d, 1H: 5ε$_1$), 7.10 to 7.55 (up, 8H: 6γ+6δ+6ε+=CH—O—+1'H$_5$+1'H$_4$), 7.85 (dd, 1H×0.85: 1'H$_6$ 1st isomer), 8 (dd, 1H×0.15: 1'H$_6$ 2nd isomer).

The 5δ-hydroxymethylenepristinamycin I$_A$ can be prepared as described in Example 44.

EXAMPLE 50

By following a procedure analogous to the method described in Example 48, but stirring for 20 hours, the 5δ-(3-dimethylaminopropyl)thiomethylenepristinamycin I$_A$ described above in Example 30 is prepared from 5δ-chloromethylenepristinamycin I$_A$.

The starting material can be prepared in the following manner:

A stream of chlorine gas is passed through a solution of triphenyl phosphite (1.3 cc) in methylene chloride (25 cc) until a persistent greenish yellow colour is obtained, the temperature being kept at between −20° C. and −15° C. Triphenyl phosphite (6 drops) is then added in order to decolourize the solution, this being followed by 5δ-hydroxymethylenepristinamycin I$_A$ (4.1 g), the temperature still being kept at between −20° C. and −15° C. The solution obtained is stirred for 1 hour at −15° C. and a solution of pyridine (0.4 cc) in methylene chloride (25 cc) is then added dropwise. The reaction mixture is subsequently stirred for 30 minutes at a temperature of the order of 20° C. and concentrated hydrochloric acid (d=1.19) (0.46 cc) and methylene chloride (50 cc) are then added. The mixture is washed 4 times with distilled water (100 cc in total); the organic phase is dried over magnesium sulphate and filtered and the filtrate is then concentrated to dryness under reduced pressure (2.7 kPa) at 30° C. The residue obtained is purified by "flash" chromatography [eluent: ethyl acetate]; after concentration to dryness of fractions 7 to 9 under reduced pressure (2.7 kPa) at 30° C., 5δ-chloromethylenepristinamycin I$_A$ (1.2 g) is obtained in the form of a beige powder melting at about 190° C.

NMR spectrum: 0.55 (dd, 1H: 5β$_2$), 2.45 (d, 1H: 5β$_1$), 3.45 (dd, 1H: 5ε$_2$), 5.30 (d, 1H: 5α), 5.45 (d, 1H: 5ε$_1$), 7.15 to 7.60 (up, 8H: 6γ+6δ+6ε+1'H$_4$+1'H$_5$+=CH—Cl), 7.85 (dd, 1H: 1'H$_6$).

The present invention includes within its scope pharmaceutical compositions comprising a compound of the formula (I), in the free form or in the form of an addition salt with a pharmaceutically acceptable acid, or if appropriate, a pharmaceutically acceptable base, in association with a pharmaceutically acceptable diluent or adjuvant.

Other pharmaceutically compatible products, which may be inert or physiologically active, may be present. The compositions can be administered parenterally, orally rectally or topically.

Sterile compositions for parenteral administration are preferably suspensions, emulsions or aqueous or non-aqueous solutions. Water, propylene glycol, a polyethylene glycol, vegetable oils, in particular olive oil, injectable organic esters, e.g. ethyl oleate, or other suitable organic solvents can be employed as the solvent or vehicle. These compositions can also contain adjuvants, in particular wetting agents, agents for imparting isotonicity, emulsifiers, dispersants and stabilizers. Sterilization can be carried out in several ways, e.g. by filtration under aseptic conditions, by incorporating sterilizing agents into the composition, by irradiation or by heating. The compositions can also be prepared in the form of sterile solid compositions which can be dissolved in an injectable sterile medium at the time of use.

The compositions for rectal administration are suppositories or rectal capsules, which contain, in addition to the active principle, excipients such as cocoa butter, semi-synthetic glycerides or polyethylene glycols.

Tablets, pills, powders or granules can be used as solid compositions for oral administration. In these compositions, the active product according to the invention (if appropriate in association with another pharmaceutically compatible product) is mixed with one or more inert diluents or adjuvants such as sucrose, lactose or starch. These compositions can also comprise substances other than diluents, e.g. a lubricant such as magnesium stearate.

Solutions, suspensions, syrups and elixirs containing inert diluents such as water or paraffin oil, and pharmaceutically acceptable emulsions, can be used as liquid compositions for oral administration. These compositions can also comprise substances other than diluents, e.g. wetting, sweetening or flavouring products.

The compositions for topical administration can be e.g. creams, ointments, lotions, eye lotions, mouthwashes, nose drops or aerosols.

In human therapy, the compounds of the invention are particularly useful in the treatment of infections of bacterial origin. The doses depend on the desired effect and the duration of the treatment. For an adult, they are generally between 2000 and 4000 mg per day, administered parenterally, in particular intravenously by slow perfusion.

In general, the physician will determine the dosage which he considers to be most appropriate as a function of the age, the weight and all the other factors peculiar to the subject to be treated.

The Examples which follow illustrate compositions according to the invention.

EXAMPLE A

An injectable solution for perfusion, containing 5 g/liter of active product and having the following composition, is prepared by the usual technique:

5δ-(3-dimethylaminopropyl)thiomethylpristinamycin I$_A$: 5 g
0.1N aqueous solution of hydrochloric acid: 50 cc
distilled water: q.s. 1000 cc

EXAMPLE B

An injectable solution for perfusion, containing 5 g/liter of active product and having the following composition, is prepared by the usual technique:

5δ-[2-(4-methylpiperazin-1-yl)ethyl]thiomethylpristinamycin I$_A$: 5 g
0.1N aqueous solution of hydrochloric acid: 48 cc
distilled water: q.s. 1000 cc

We claim:
1. A synergistine of the formula:

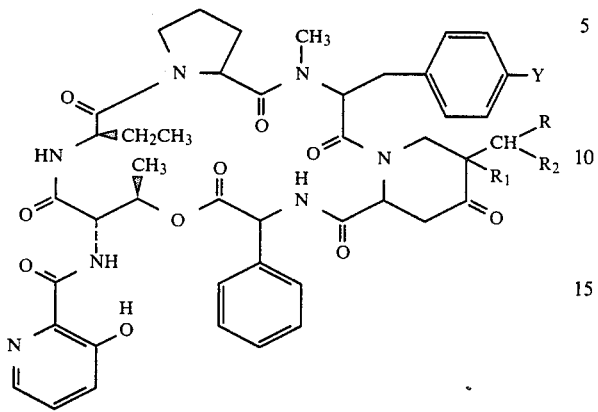

in which Y represents hydrogen or dimethylamino and
(a) $R_1$ and $R_2$ each represent hydrogen, and R represents a member of the class consisting of pyrrolidin-3-ylthio, alkyl-substituted pyrrolidin-3-ylthio, piperidin-3-ylthio, alkyl-substituted piperidin-3-ylthio, piperidin-4-ylthio, and alkyl-substituted piperidin-4-ylthio, and alkylthio substituted by one to two radicals selected from the class consisting of:
hydroxysulphonyl,
alkylamino,
mercaptoalkylamino,
dialkylaminoalkylamino,
dialkylamino,
N-alkyl-N-mercaptoalkyl-amino,
N-alkyl-N-dialkylaminoalkyl-amino
piperazino,
alkyl-piperazino,
mercaptoalkyl-piperazino,
morpholino,
thiomorpholino,
piperidino,
pyrrolidin-1-yl,
piperidin-2-yl,
N-alkyl-piperidin-2-yl,
piperidin-3-yl,
N-alkyl-piperidin-3-yl,
piperidin-4-yl,
N-alkyl-piperidin-4-yl,
pyrrolidin-2-yl,
N-alkylpyrrolidin-2-yl,
pyrrolidin-3-yl, and
N-alkyl-pyrrolidin-3-yl; or
(b) $R_1$ and $R_2$ together form a valence bond, and R represents a member of the class consisting of:
pyrrolidin-3-ylamino, N-alkyl-pyrrolidin-3-ylamino, piperidin-3-ylamino, N-alkyl-piperidin-3-ylamino, piperidin-4-ylamino, N-alkyl-piperidin-4-ylamino, pyrrolidin-3-yloxy, N-alkyl-pyrrolidin-3-yloxy, piperidin-3-yloxy, N-alkyl-piperidin-3-yloxy, piperidin-4-yloxy N-alkyl-piperidin-4-yloxy pyrrolidin-3-ylthio, N-alkyl-pyrrolidin-3-ylthio piperidin-3-ylthio, N-alkyl-piperidin-3-ylthio piperidin-4-ylthio N-alkyl-piperidin-4-ylthio, and alkylamino, alkoxy and alkylthio radicals substituted by one to two radicals selected from the class consisting of:
hydroxysulphonyl
alkylamino
dialkylaminoalkylamino
dialkylamino
N-alkyl-N-dialkylaminoalkyl-amino
trialkylammonio
imidazol-4-yl
imidazol-5-yl
piperazino
alkylpiperazino
mercaptoalkylpiperazino
morpholino
thiomorpholino
piperidino
pyrrolidin-1-yl
piperidin-2-yl
piperidin-3-yl
piperidin-4-yl
pyrrolidin-2-yl
pyrrolidin-3-yl
N-alkyl-pyrrolidin-2-yl, and
N-alkyl-pyrrolidin-3-yl
the aforesaid alkyls and alkyl portions of said radicals containing 1 to 5 carbon atoms each in a linear or branched chain, and its isomeric forms where such exist, and mixtures thereof, and its pharmaceutically acceptable acid addition salts.

2. A synergistine according to claim 1 in which Y is a hydrogen atom or a dimethylamino radical and—either $R_1$ and $R_2$ each represent a hydrogen atom and R represents a piperidin-4-ylthio radical unsubstituted or substituted by an alkyl radical, or an alkylthio radical substituted by one or two dialkylamino radicals, each optionally substituted by a mercapto radical or alkylpiperazino or mercaptoalkylpiperazino radicals or $R_1$ and $R_2$ together form a valence bond and R represents a piperidin-3-ylamino, piperidin-4-ylamino, piperidin-3-ylthio, or piperidin-4-ylthio unsubstituted or substituted on the nitrogen atom of the ring by an alkyl radical, or alternatively R represents an alkylamino, alkoxy or alkylthio radical substituted by one or two hydroxysulphonyl radicals, alkylamino or diakylamino radicals, optionally substituted by another dialkylamino radical, or trialkylammonio, imidazol-4-yl, or imidazol-5-yl alkylpiperazino, morpholino, piperidino, pyrrolidinyl or N-alkylpyrrolidinyl radicals and its pharmaceutically acceptable salts.

3. A synergistine according to claim 1 in which Y is a hydrogen atom or a dimethylamino radical and—either $R_1$ and $R_2$ each represent a hydrogen atom and R represents an alkylpiperidin-4-ylthio radical or an alkylthio radical substituted by one or two dialkylamino or alkylpiperazino radicals, or $R_1$ and $R_2$ together form a valence bond and R represents a 1-alkylpiperidin-4-ylamino radical, or alternatively R represents a straight-chain alkylamino radical substituted by an alkylamino or dialkylamino radical of which the alkyl parts may form, with the nitrogen atom to which they are attached, a heterocycle chosen from pyrrolidin-1-yl, piperidino and 4-alkylpiperazino, or by a 1-alkyl pyrrolidin-2-yl radical, or alternatively R represents a straight-chain alkylthio radical substituted by a 4-alkylpiperazino radical or represents a 5-dialkylaminopent-2-yl radical and its pharmaceutically acceptable salts.

4. A synergistine according to claim 1 in which Y is a hydrogen atom or a dimethylamino radical and
$R_1$ and $R_2$ each represent a hydrogen atom and R represents an alkylpiperidin-4-ylthio radical or an alkylthio radical substituted by one or two dialkylamino radicals or by an alkylpiperazino radical, or alternatively R$_1$ and R$_2$ together form a valence bond and R represents a 1-alkylpiperidin-4-ylamino radical, it being understood that the said alkyl portions and radicals are linear or branched and contain 1 to 3 carbon atoms each and its pharmaceutically acceptable salts.

5. A synergistine according to claim 1 which is 5δ-(3-dimethylaminopropyl)thiomethylpristinamycin I$_A$ and its pharmaceutically acceptable salts.

6. A synergistine according to claim 1 which is 5δ-[2-(4-methylpiperazin-1-yl)ethyl]thiomethylpristinamycin I$_A$ and its pharmaceutically acceptable salts.

7. A synergistine according to claim 1 which is 5δ-[3-(4-methylpiperazin-1-yl)propyl]thiomethylpristinamycin I$_A$ and its pharmaceutically acceptable salts.

8. A synergistine according to claim 1 which is 5δ-[1,3-bis(dimethylamino)prop-2-yl]thiomethylpristinamycin I$_A$ and its pharmaceutically acceptable salts.

9. A synergistine according to claim 1 which is 5δ-(1-methylpiperidin-4-yl)aminomethylenepristinamycin I$_A$; and its pharmaceutically acceptable salts.

10. A pharmaceutical composition useful for treating bacterial infections which contains an effective amount of at least one synergistine according to claim 1, in association with one or more compatible, pharmaceutically acceptable diluents or adjuvants.

11. A composition according to claim 10 in the form of a sterile injectable solution.

12. A method of treating a bacterial infection in a living subject which comprises administering to said subject an effective amount of a synergistine according to claim 1.

* * * * *